United States Patent
Hatta et al.

(10) Patent No.: US 10,768,591 B2
(45) Date of Patent: Sep. 8, 2020

(54) BEHAVIOR IDENTIFICATION DEVICE, AIR CONDITIONER, AND ROBOT CONTROL DEVICE

(71) Applicant: Mitsubishi Electric Corporation, Chiyoda-ku (JP)

(72) Inventors: Toshiyuki Hatta, Chiyoda-ku (JP); Shotaro Miwa, Chiyoda-ku (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 321 days.

(21) Appl. No.: 15/569,818

(22) PCT Filed: Sep. 3, 2015

(86) PCT No.: PCT/JP2015/075067
§ 371 (c)(1),
(2) Date: Oct. 27, 2017

(87) PCT Pub. No.: WO2017/037915
PCT Pub. Date: Mar. 9, 2017

(65) Prior Publication Data
US 2018/0136622 A1 May 17, 2018

(51) Int. Cl.
*G05B 19/042* (2006.01)
*A61B 5/11* (2006.01)
(Continued)

(52) U.S. Cl.
CPC ........... *G05B 19/042* (2013.01); *A61B 5/11* (2013.01); *B25J 9/1651* (2013.01); *F24F 11/63* (2018.01);
(Continued)

(58) Field of Classification Search
CPC .............. G05B 19/042; G05B 19/0428; G05B 2219/33051; F24F 11/63; F24F 2120/14; A61B 5/11; B25J 9/1651
See application file for complete search history.

(56) References Cited

U.S. PATENT DOCUMENTS 6,126,595 A * 10/2000 Amano ................... A61B 5/18
   600/300
8,489,253 B2 * 7/2013 Shirakata ............... G08B 21/06
   340/576
(Continued)

FOREIGN PATENT DOCUMENTS

CN     103984315 A     8/2014
CN     104566868 A     4/2015
(Continued)

OTHER PUBLICATIONS

International Search Report dated Nov. 24, 2015 in PCT/JP2015/075067, filed on Sep. 3, 2015.
(Continued)

*Primary Examiner* — Nicholas Kiswanto
(74) *Attorney, Agent, or Firm* — Xsensus LLP

(57) ABSTRACT

The present invention provides a behavior identification device that can identify various behaviors without specifically defining a component constituting a behavior in advance. The behavior identification device comprising:
  a sensor-value obtaining unit (10) that obtains the sensor value and calculates a sensor value distribution that is a distribution of the sensor value measured within a predetermined time;
  a component database (42) that stores therein a set of basic distributions that are basic components constituting the sensor value distribution;
  a ratio calculating unit (21) that calculates a first component ratio that is a ratio of each of the basic distributions included in the sensor value distribution;
(Continued)

a component ratio database (43) that stores therein a second component ratio that is the ratio determined in association with a behavior to be identified; and an identification unit (22) that compares the first component ratio to the second component ratio to identify the behavior, wherein the basic distribution is calculated as a sensor value distribution that is a base when each sensor value distribution is assumed to be a vector based on a set of the sensor value distributions obtained in advance for each of a plurality of types of the behavior.

19 Claims, 23 Drawing Sheets

(51) Int. Cl.
*F24F 11/62* (2018.01)
*B25J 9/16* (2006.01)
*F24F 120/14* (2018.01)
*F24F 11/63* (2018.01)

(52) U.S. Cl.
CPC ...... *F24F 2120/14* (2018.01); *G05B 19/0428* (2013.01); *G05B 2219/33051* (2013.01)

(56) References Cited

U.S. PATENT DOCUMENTS

2008/0120025 A1  5/2008  Naitou et al.
2016/0095013 A1* 3/2016  Faivishevsky ........ H04L 67/125
                                                    370/252

FOREIGN PATENT DOCUMENTS

| CN | 104574817 A | 4/2015 |
| JP | 2008-117293 A | 5/2008 |
| JP | 2008-126908 A | 6/2008 |
| JP | 2009-039486 A | 2/2009 |
| JP | 2010-213782 A | 9/2010 |
| JP | 2011-156132 A | 8/2011 |
| JP | 2013-041323 A | 2/2013 |
| JP | 2014-212915 A | 11/2014 |

OTHER PUBLICATIONS

Office Action was dated Dec. 4, 2019 in corresponding Chinese Patent Application No. 201580081032.1. with English Translation.
Julia Seiter et al., "Discovery of activity composites using topic models: an analysis of unsupervised methods", Pervasive and Mobile Computing, vol. 15, p. 215-227.
Office Action dated Apr. 30, 2020 in corresponding Chinese Patent Application No. 201580081032.1 with English Translation.

* cited by examiner

Fig.3
(a)
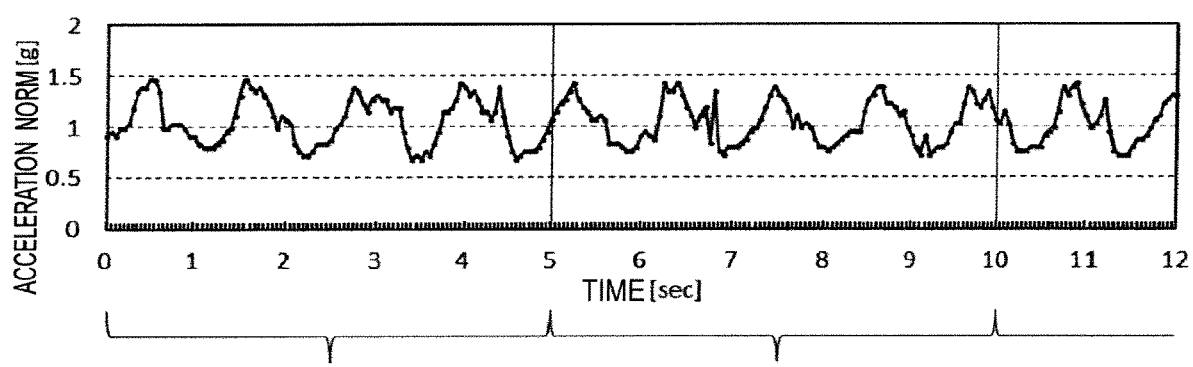
(b)
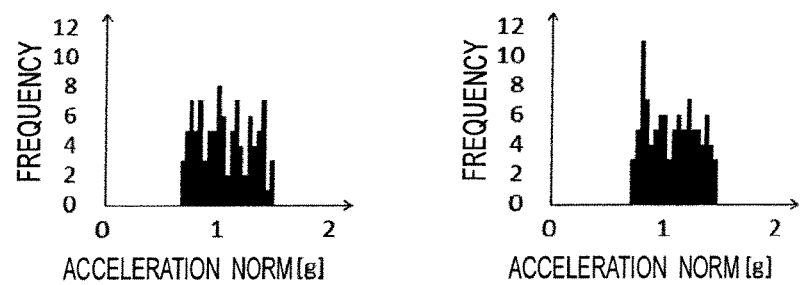

Fig.5
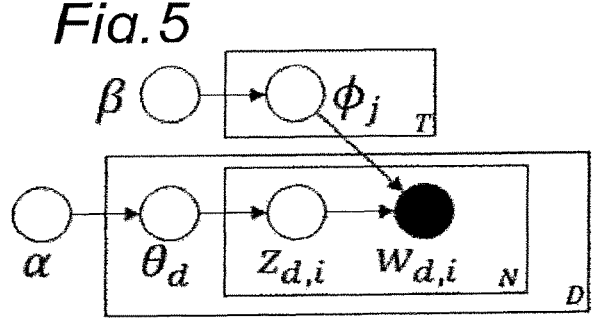
Fig.6
(a)
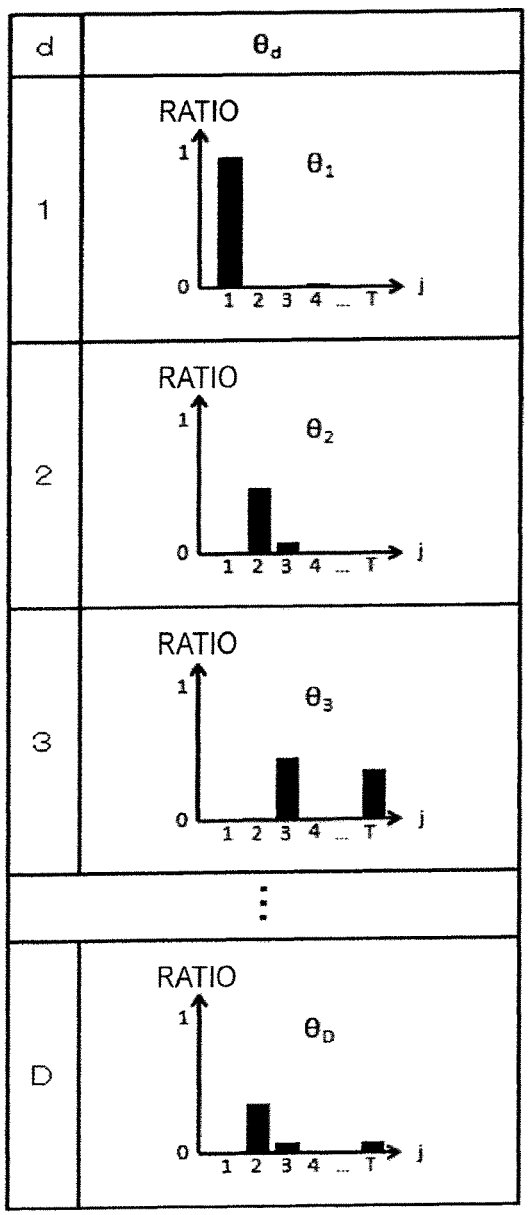
(b)
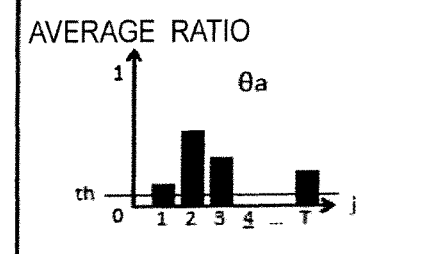

Fig.8

| d | θ_d | LABEL |
|---|---|---|
| 1 | $\theta_1$ | STOPPING |
| 2 | $\theta_2$ | WALKING |
| 3 | $\theta_3$ | RUNNING |
| ⋮ | ⋮ | ⋮ |
| D | $\theta_D$ | WALKING |

| θ2 |
|---|
| (bar chart: RATIO vs j, bar at 2) |

(b)

| d | θ_d | LABEL |
|---|---|---|
| 1 | (bar at j=1) θ₁ | STOPPING |
| 2 | (bar at j=2) θ₂ | WALKING |
| 3 | (bars at j=3, T) θ₃ | RUNNING |
| ⋮ | ⋮ | |
| D | (bar at j=2) θ_D | WALKING |

(c)

| $HI_d$ |
|---|
| 0.005 |
| 0.959 |
| 0.260 |
| ⋮ |
| 0.878 |

|  |  | MODE A | | | | |
|---|---|---|---|---|---|---|
|  |  | $\phi a_1$ | $\phi a_2$ | $\phi a_3$ | $\phi a_4$ | $\phi a_5$ |
| MODE B | $\phi b_1$ | 0.0272 | 0.0705 | 0.4905 | 0.1482 | 0.5741 |
|  | $\phi b_2$ | 0.9891 | 0.2557 | 0.0401 | 0.0988 | 0.0268 |
|  | $\phi b_3$ | 0.2271 | 0.8411 | 0.1780 | 0.6406 | 0.0895 |
|  | $\phi b_4$ | 0.0581 | 0.3383 | 0.2509 | 0.7668 | 0.3560 |
|  | $\phi b_5$ | 0.0378 | 0.1181 | 0.2419 | 0.2807 | 0.6732 |

Fig.19

| MODE A | |
|---|---|
| j | DISTRIBUTION NAME |
| 1 | $\phi c_1$ |
| 2 | $\phi c_2$ |
| 3 | $\phi a_3$ |
| 4 | $\phi c_3$ |
| 5 | $\phi a_5$ |

| MODE B | |
|---|---|
| j | DISTRIBUTION NAME |
| 1 | $\phi b_1$ |
| 2 | $\phi c_1$ |
| 3 | $\phi c_2$ |
| 4 | $\phi c_3$ |
| 5 | $\phi b_5$ |

Fig.20
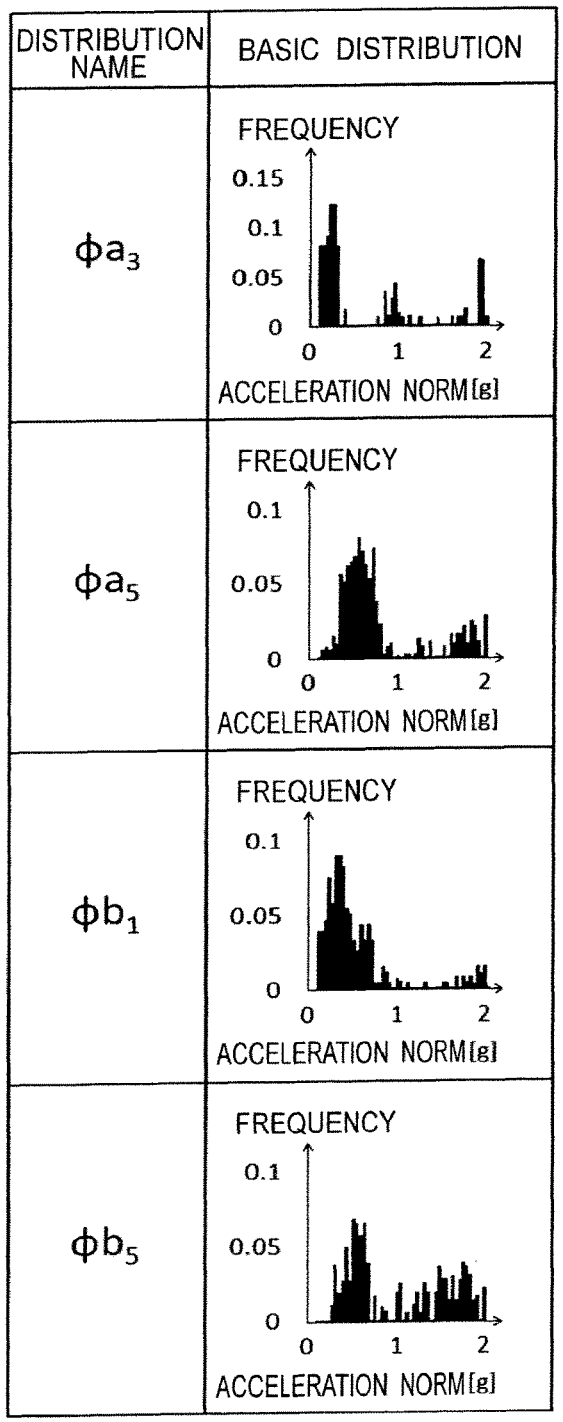
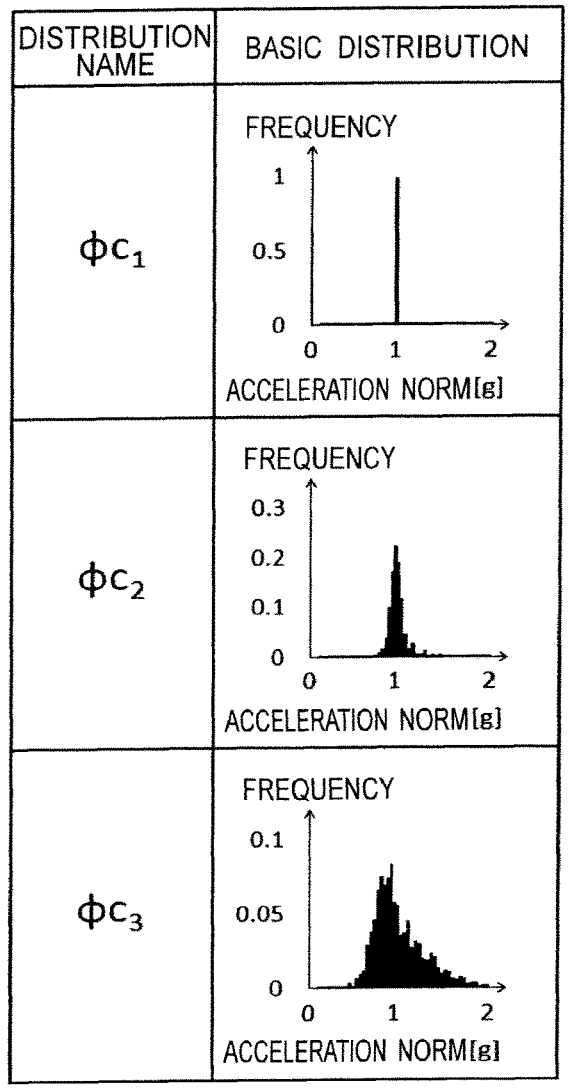

Fig.21

| MODE A | | |
|---|---|---|
| d | $\theta_d$ | LABEL |
| 1 | $\theta_1$ | STOPPING |
| 2 | $\theta_2$ | WALKING |
| ⋮ | ⋮ | ⋮ |
| Da | $\theta_{Da}$ | WALKING |

| MODE B | | |
|---|---|---|
| d | $\theta_d$ | LABEL |
| 1 | $\theta_1$ | STOPPING |
| 2 | $\theta_2$ | RUNNING |
| ⋮ | ⋮ | ⋮ |
| Db | $\theta_{Db}$ | WALKING |

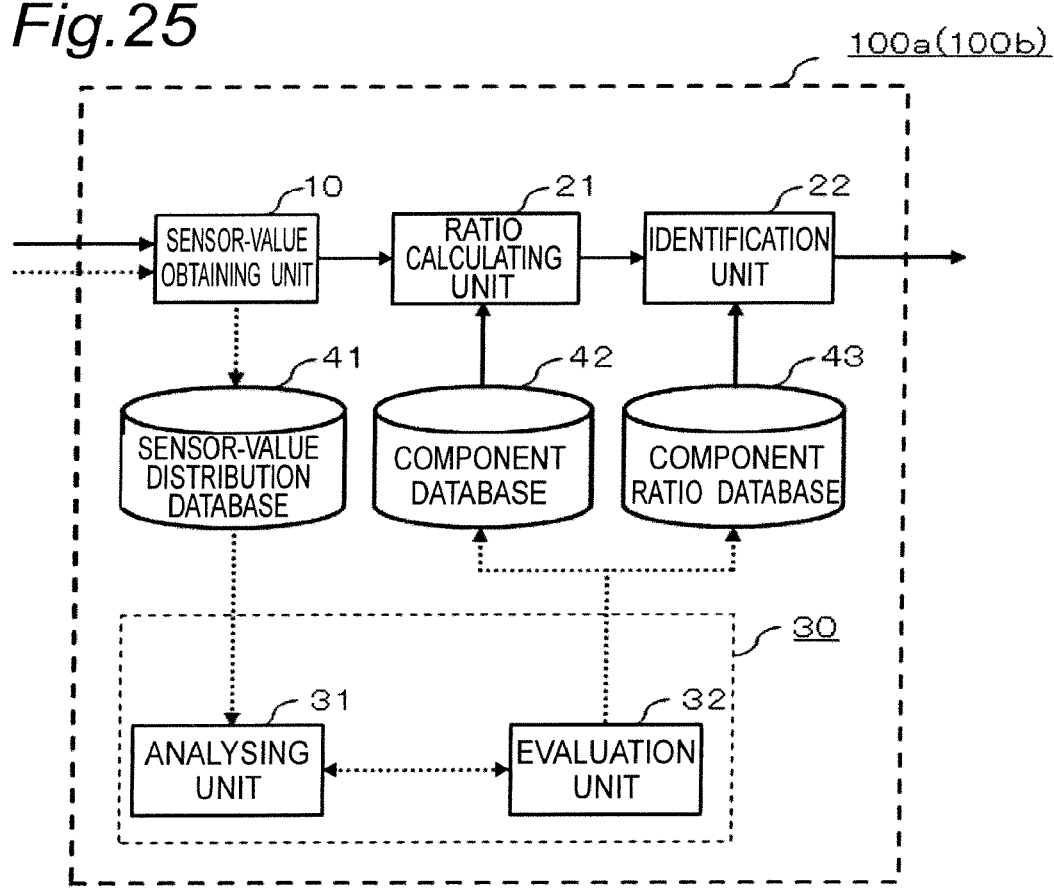

Fig.27
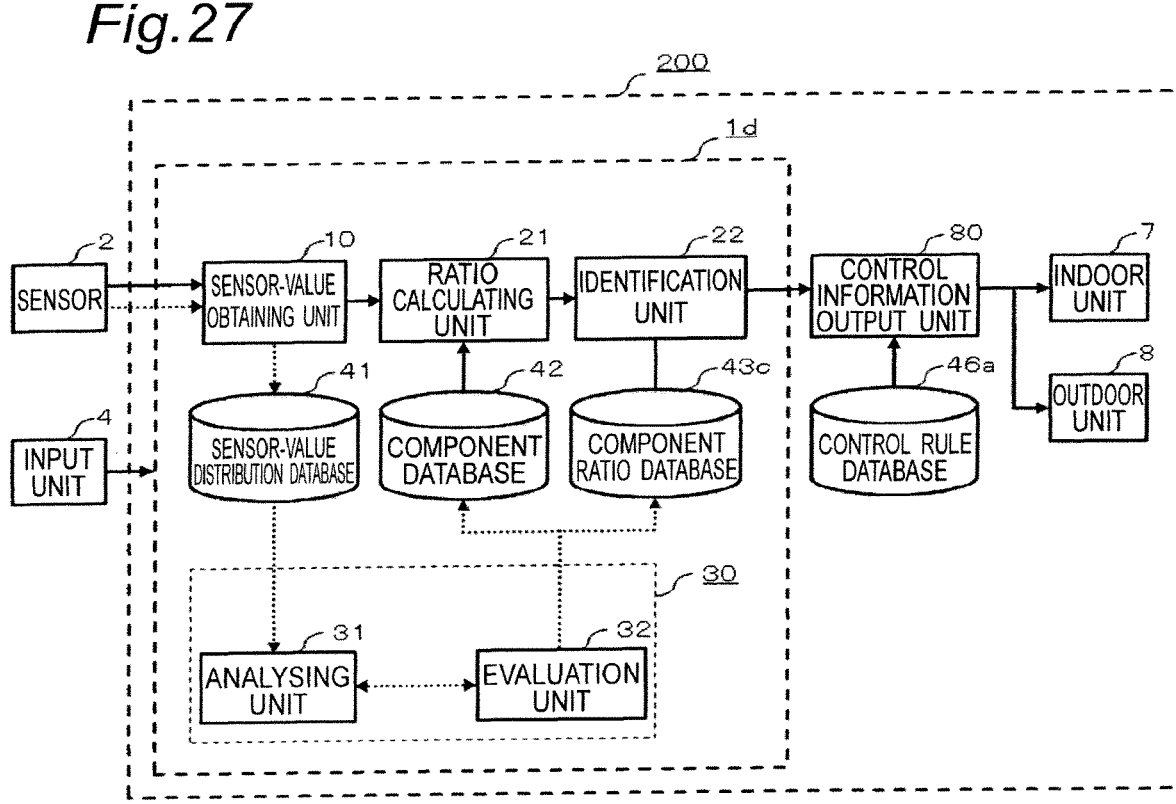
Fig.28
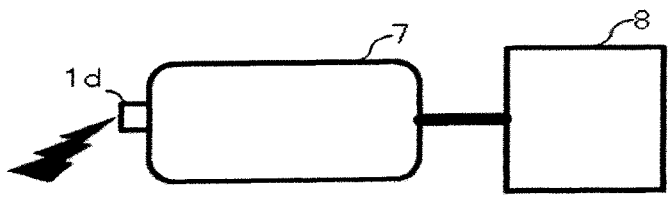
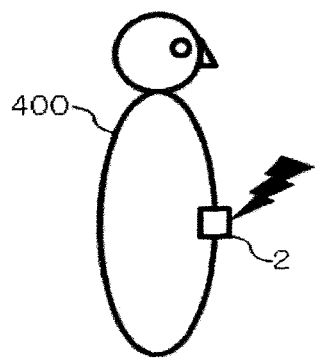

Fig.29

| d | $\theta_d$ | BIOLOGICAL INDEX |
|---|---|---|
| 1 | $\theta_1$ | 1.0 |
| 2 | $\theta_2$ | 3.0 |
| 3 | $\theta_3$ | 8.0 |
| ⋮ | ⋮ | ⋮ |
| D | $\theta_D$ | 3.0 |

Fig.30

| RATIO IDENTIFICATION RESULT | CONTROL RULE |
|---|---|
|  | NOT DIRECTLY BLOWING ON TARGET |
| 1.0 METs OR MORE AND LESS THAN 8.0 METs | SAME AS NORMAL |
| 8.0 METs OR MORE | DIRECTLY BLOWING ON TARGET |

Fig.33

| d | θ_d | LABEL |
|---|---|---|
| 1 | RATIO vs j, θ_1 | SAFE BEHAVIOR |
| 2 | RATIO vs j, θ_2 | SAFE BEHAVIOR |
| ⋮ | ⋮ | |
| D−1 | RATIO vs j, θ_{D−1} | DANGEROUS BEHAVIOR |
| D | RATIO vs j, θ_D | DANGEROUS BEHAVIOR |

Fig.34

| IDENTIFICATION RESULT | CONTROL RULE |
|---|---|
| SAFE BEHAVIOR | NORMAL OPERATION |
| DANGEROUS BEHAVIOR | EMERGENCY STOP |
| DEVIANT BEHAVIOR | REDUCE OPERATING SPEED ASK FOR CHECK-UP |

BEHAVIOR IDENTIFICATION DEVICE, AIR CONDITIONER, AND ROBOT CONTROL DEVICE

TECHNICAL FIELD

The present invention relates to a behavior identification device that identifies a behavior of a target, an air conditioner using such a behavior identification device, and a robot control device using such a behavior identification device.

BACKGROUND ART

Conventional behavior identification devices use sensor values measured by various sensors incorporated in wearable terminals or portable terminals to identify behaviors of a target. For example, acceleration sensors, angular velocity sensors, heart rate sensors, and the like are used for the sensors. There has been conventionally proposed a behavior identification device in which a designer defines in advance component behaviors constituting a behavior and identifies the component behaviors using sensor values so as to identify the behavior.

For example, a behavior identification device described in Patent Document 1 identifies a component behavior using an identification device that is configured in advance for each component behavior and then identifies a behavior using a sequence of identification results of component behaviors. A behavior identification device described in Patent Document 2 identifies a component behavior that is selected depending on the performance of the device, resources, or the like so as to efficiently use an identification device that is configured in advance for each component behavior, and then identifies a behavior using combinations of evaluation values, which are identification results of component behaviors. As described above, the behavior identification devices described in Patent Documents 1 and 2 do not identify a behavior as a single behavior but identify a behavior as a combination of component behaviors constituting the behavior using a sequence of identification results of component behaviors or a combination of evaluation values.

PRIOR ART DOCUMENTS

Patent Documents

Patent Document 1: JP 2010-213782 A
Patent Document 2: JP 2011-156132 A

SUMMARY OF THE INVENTION

Problems to be Solved by the Invention

A conventional behavior identification device needs to specifically define component behaviors constituting a behavior in advance and to configure an identification device for each of the component behaviors. That is, in the conventional behavior identification device, the behavior, which is an identification target, is limited to a behavior in which component behaviors constituting the behavior are definable in advance. However, it is thought that, for example, behaviors in daily life of people are constituted by complicated combinations of component behaviors, and thus it is difficult for a designer to specifically define component behaviors constituting such a behavior in advance.

The present invention has been achieved to solve the above problems, and an object of the invention is to provide a behavior identification device that can identify various behaviors without specifically defining a component constituting a behavior in advance by a designer.

Means for Solving the Problems

A behavior identification device according to the present invention identifies a behavior of a target using a sensor value measured by a sensor for the behavior of the target. The behavior identification device includes a sensor-value obtaining unit that obtains a sensor value and calculates a sensor value distribution that is a distribution of the sensor value measured within a predetermined time, a component database that stores therein a set of basic distributions that are basic components constituting the sensor value distribution, a ratio calculating unit that calculates a first component ratio that is a ratio of each of the basic distributions included in the sensor value distribution, a component ratio database that stores therein a second component ratio determined in association with a behavior to be identified, and an identification unit that compares the first component ratio to the second component ratio to identify the behavior. The basic distribution is calculated as a sensor value distribution that is a base when each sensor value distribution is assumed to be a vector based on a set of the sensor value distributions obtained in advance for each of a plurality of types of the behavior.

Effects of the Invention

According to the behavior identification device of the present invention, the basic distribution stored in the component database is calculated as a sensor value distribution that is a base when each sensor value distribution is assumed to be a vector based on a set of the sensor value distributions obtained in advance for each of a plurality of types of the behavior. It is thus unnecessary for a designer to specifically define components constituting a behavior in advance. In addition, it is possible to identify a behavior that cannot be specifically defined by the designer.

BRIEF DESCRIPTION OF THE DRAWINGS

FIGS. 3A and 3B are diagrams for explaining an operation of a sensor-value obtaining unit in the behavior identification device according to the first embodiment of the present invention.

FIG. 5 shows a graphical model of a generation process assumed in an analysing unit in the behavior identification device according to the first embodiment of the present invention.

FIGS. 6A and 6B are diagrams for explaining an operation of an evaluating unit in the behavior identification device according to the first embodiment of the present invention.

FIG. 8 is a diagram for explaining a data structure of a component ratio database in the behavior identification device according to the first embodiment of the present invention.

FIGS. 9A, 9B, and 9C are diagrams for explaining an operation of an identification unit in the behavior identification device according to the first embodiment of the present invention.

FIG. 19 is a diagram for explaining a data structure of a mode corresponding database in the behavior identification device according to the second embodiment of the present invention.

FIG. 20 is a diagram for explaining a data structure of a component database in the behavior identification device according to the second embodiment of the present invention.

FIG. 21 is a diagram for explaining a data structure of a component ratio database in the behavior identification device according to the second embodiment of the present invention.

FIG. 25 shows an example of a configuration of an action identification unit in the behavior identification device according to the third embodiment of the present invention.

FIG. 26 is a diagram for explaining a data structure of a combining rule database in the behavior identification device according to the third embodiment of the present invention.

FIG. 27 shows an example of a configuration of an air conditioner according to a fourth embodiment of the present invention.

FIG. 28 is a diagram for explaining a usage example of the air conditioner according to the fourth embodiment of the present invention.

FIG. 29 is a diagram for explaining a data structure of a component ratio database in the air conditioner according to the fourth embodiment of the present invention.

FIG. 30 is a diagram for explaining a data structure of a control rule database in the air conditioner according to the fourth embodiment of the present invention.

FIG. 33 is a diagram for explaining a data structure of a component ratio database in the robot control device according to the fifth embodiment of the present invention.

FIG. 34 is a diagram for explaining a data structure of a control rule database in the robot control device according to the fifth embodiment of the present invention.

EMBODIMENTS OF THE INVENTION

First Embodiment

Figure 1:
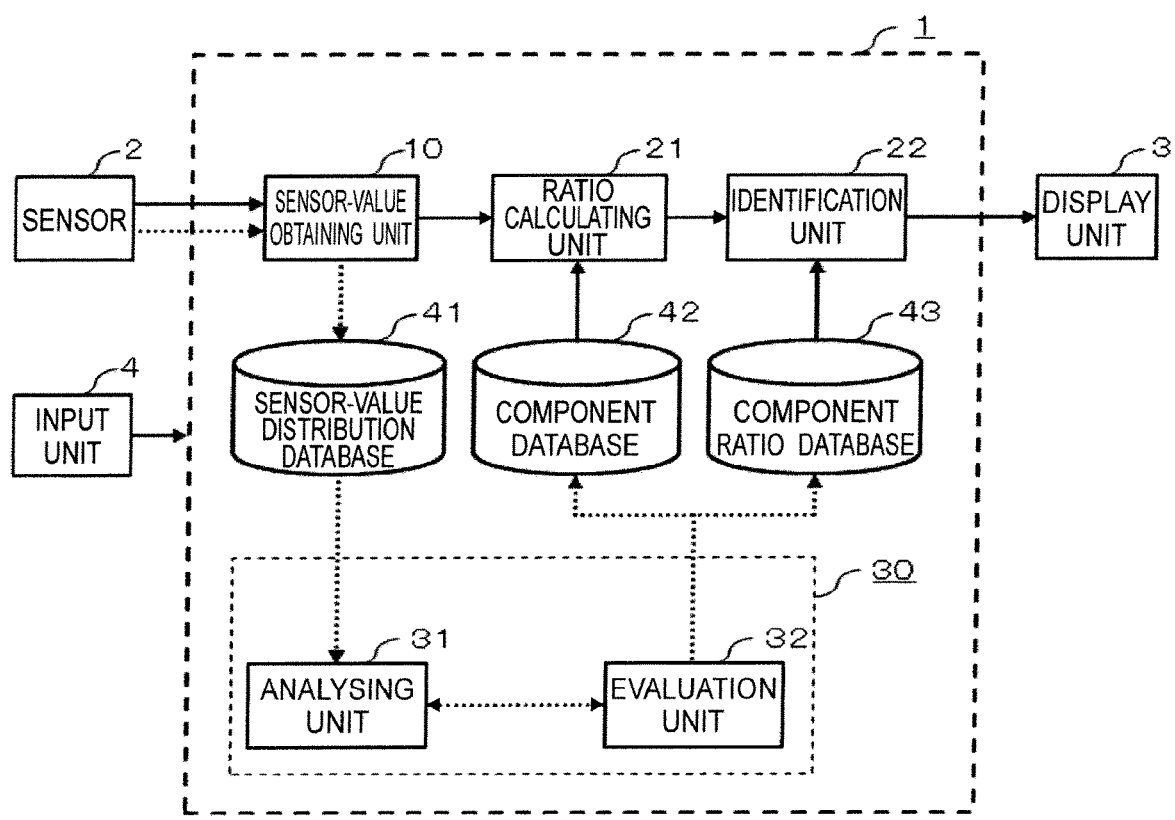
FIG. 1 shows an example of a configuration of a behavior identification device according to a first embodiment of the present invention.

FIG. 1 shows an example of a configuration of a behavior identification device 1 according to a first embodiment of the present invention. The behavior identification device 1 identifies a behavior of a target. For example, the behavior identification device 1 is incorporated in a wearable terminal or a portable terminal together with a sensor 2, a display unit 3, and an input unit 4, and is attached to or carried by the target. "Behavior" collectively means the behavior, action, and posture of a person and the like, and examples of the behavior include "stopping", "walking", and "running".

The overall configuration of the behavior identification device 1 is described with reference to FIG. 1. The behavior identification device 1 includes a sensor-value obtaining unit 10, a ratio calculating unit 21, an identification unit 22, a basic distribution generating unit 30, a sensor-value distribution database 41, a component database 42, and a component ratio database 43. In addition, the basic distribution generating unit 30 includes an analysing unit 31 and an evaluating unit 32. The sensor 2, the display unit 3, and the input unit 4 are connected to the behavior identification device 1. The behavior identification device 1 identifies a behavior using a sensor value measured by the sensor 2 and displays an identification result on the display unit 3.

Before an operation of the behavior identification device 1 is described, the sensor 2 is described. In the present embodiment, the sensor 2 is a three-axis acceleration sensor that is attached to, for example, the waist of a target, and measures three-axis acceleration values ax, ay, and az for a behavior of the target. In addition, the sensor 2 calculates a norm |a| of the three-axis acceleration values ax, ay, and az by formula (1), and outputs the norm as a sensor value every 50 milliseconds.

[Formula 1]

$$|a|=\sqrt{ax^2+ay^2+az^2} \qquad (1)$$

Figure 2:
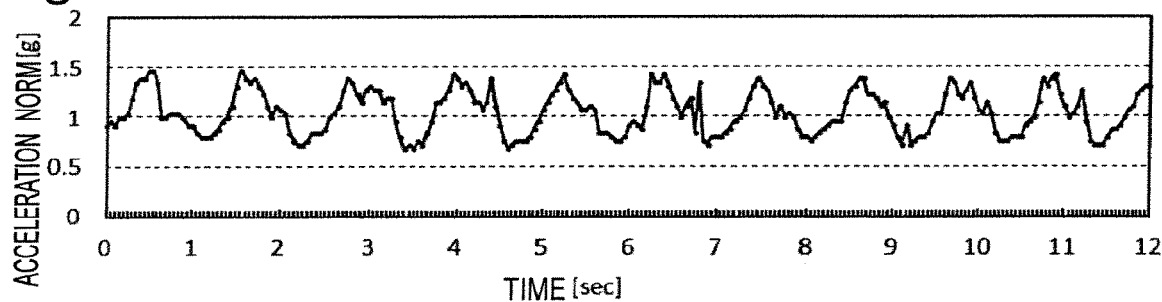
FIG. 2 shows an example of a sensor value measured by a sensor according to the first embodiment of the present invention.

FIG. 2 shows an example of a sensor value measured by the sensor 2 according to the present embodiment. In FIG. 2, the vertical axis indicates an acceleration norm, which is a sensor value, and the horizontal axis indicates a sensor-value obtaining time. While the first embodiment describes a case where a three-axis acceleration sensor is used as the sensor 2 and is attached to the waist of a target, the present invention is not limited thereto, and any sensor that can measure a sensor value corresponding to a behavior of the target can be used. In addition to the three-axis acceleration sensor, for example, an angular velocity sensor, a position sensor, an air pressure sensor, and a heart rate sensor can be used.

Next, the operation of the behavior identification device 1 is described. The behavior identification device 1 operates in two phases, that is, a generation phase and an identification phase. In FIG. 1, broken line arrows indicate the relationships between blocks in the generation phase, whereas solid line arrows indicate the relationships between the blocks in the identification phase. An operation of the behavior identification device 1 in the generation phase is described first. In the generation phase, the sensor-value obtaining unit 10 obtains a sensor value from the sensor 2 and calculates a sensor value distribution $h_d$ that is a distribution of sensor values measured by the sensor 2 within a predetermined time. d denotes a data number for identifying each of a plurality of sensor value distributions.

FIGS. 3A and 3B are diagrams for explaining an operation of the sensor-value obtaining unit 10 in the behavior identification device 1 according to the present embodiment. FIG. 3A is a diagram in which sensor values output from the sensor 2 are divided for each predetermined time. In FIG. 3A, the vertical axis indicates an acceleration norm, which is a sensor value, and the horizontal axis indicates a sensor-value obtaining time. The predetermined time is defined as five seconds in the present embodiment. The sensor-value obtaining unit 10 quantizes the norm of three-axis acceleration values, which is a sensor value output from the sensor 2, every 0.04 g from 0.04 g to 2.00 g and calculates a histogram (a frequency distribution of occurrence) of sensor values within a predetermined time. The generated histogram is thus a sensor value distribution. That is, each sensor value distribution $h_d$ is a histogram in which a quantized sensor value is set as a class (a bin).

The sensor 2 obtains a sensor value every 50 milliseconds in the present embodiment, and thus 100 sensor values are obtained within a predetermined time, that is, five seconds. FIG. 3B shows an example of a distribution of obtained sensor values. In FIG. 3B, the horizontal axis indicates a sensor value and the vertical axis indicates the frequency of occurrence (the measurement frequency) of a sensor value. In FIG. 3B, a histogram on the left side is a distribution of sensor values obtained from 0 to 5 seconds, whereas a histogram on the right side is a distribution of sensor values obtained from 5 to 10 seconds.

Figure 4:
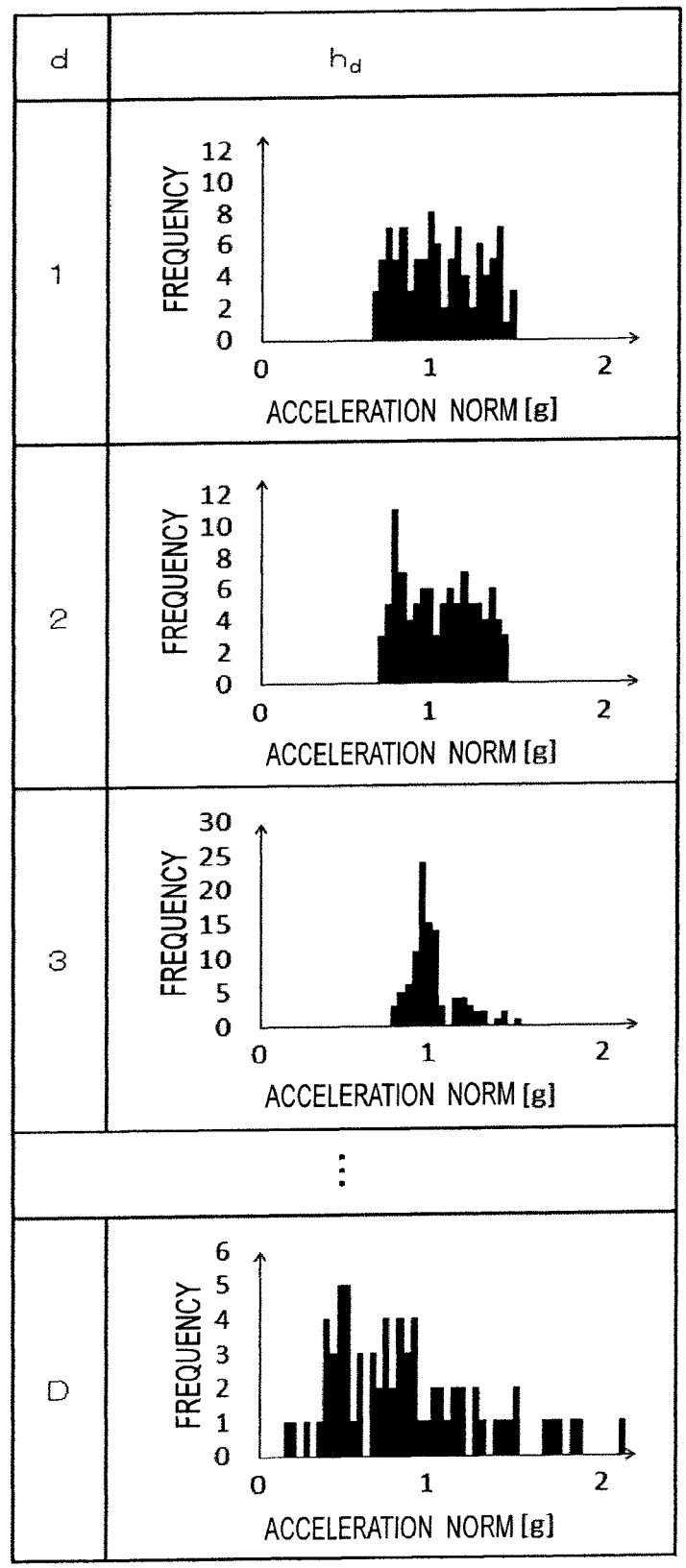
FIG. 4 is a diagram for explaining a data structure of a sensor-value distribution database in the behavior identification device according to the first embodiment of the present invention.

Next, the sensor-value distribution database 41 is described. The sensor-value distribution database 41 stores therein a set of sensor value distributions $h_d$ generated by the sensor-value obtaining unit 10. FIG. 4 is a diagram for explaining a data structure of the sensor-value distribution database 41 in the behavior identification device 1 according to the present embodiment. In FIG. 4, the sensor-value distribution database 41 stores therein D sensor value distributions. As described above, a data number d is given to each of the sensor value distributions. The sensor value distribution is a histogram and thus is represented as a set of frequencies of occurrence (measurement frequencies) of each sensor value. That is, $h_d=\{h_d(1), h_d(2), h_d(3), \ldots, h_d(V)\}$. $h_d(v)$ denotes the frequency of occurrence (the measurement frequency) of a sensor value corresponding to the vth class in the dth sensor value distribution. V denotes the number of classes (bins) of a histogram. When quantization is performed every 0.04 g from 0.04 g to 2.00 g, V=50.

Next, the basic distribution generating unit 30 is described. The basic distribution generating unit 30 includes the analysing unit 31 and the evaluating unit 32. The analysing unit 31 is described first. The analysing unit 31 estimates a basic distribution and a component ratio based on a set of sensor value distributions stored in the sensor-value distribution database 41. The basic distribution is a distribution of a basic component that constitutes a sensor value distribution. The component ratio is a ratio of each basic distribution included in a sensor value distribution.

In the first embodiment, the analysing unit 31 estimates a basic distribution $\varphi_j$ constituting a sensor value distribution and a component ratio $\theta_{d,j}$ that is a ratio of each basic distribution included in a sensor value distribution using Latent Dirichlet Allocation (LDA). j denotes a basic distribution number, which is an integer from 1 to T. T denotes the number of basic distributions constituting a sensor value distribution. As described above, d denotes the data number of a sensor value distribution stored in the sensor-value distribution database 41, which is an integer from 1 to D. As described above, D denotes the number of sensor value distributions stored in the sensor-value distribution database 41. That is, the component ratio $\theta_{d,j}$ indicates a ratio of the jth basic distribution included in the dth sensor value distribution. A set of component ratios in the dth sensor value distribution is denoted by $\theta_d$. That is, $\theta_d=\{\theta_{d,1}, \theta_{d,2}, \ldots, \theta_{d,T}\}$.

In the present embodiment, the analysing unit 31 performs a process assuming that a sensor value is generated by a predetermined modeled generation process. The analysing unit 31 assumes that the basic distribution $\varphi_j$ is a probability distribution when a sensor value is generated, and estimates the basic distribution $\varphi_j$ for generating a set of measured sensor values. In the present embodiment, the generation process for generating a set of sensor values is assumed by formulae (2) to (5) wherein Dir denotes a Dirichlet distribution and Mult denotes a multinomial distribution. The basic distribution $\varphi_j$ is represented as a set of frequencies of generation of each sensor value. That is, $\varphi_j=\{\varphi_j(1), \varphi_j(2), \varphi_j(3), \ldots, \varphi_j(V)\}$. $\varphi_j(v)$ denotes the frequency of generation of a sensor value corresponding to the vth class in the jth basic distribution. V denotes the number of classes (bins) of a histogram.

[Formula 2]

$$\theta_d \sim \mathrm{Dir}(\alpha) \qquad (2)$$

[Formula 3]

$$\phi_j \sim \mathrm{Dir}(\beta) \qquad (3)$$

[Formula 4]

$$z_{d,t} \sim \mathrm{Mult}(\theta_d) \qquad (4)$$

[Formula 5]

$$w_{d,t} \sim \mathrm{Mult}(\phi_{z_{d,t}}) \qquad (5)$$

In formula (2), α denotes a parameter for a Dirichlet distribution that generates a set $\theta_d$ of component ratios. In formula (3), β denotes a parameter for a Dirichlet distribution that generates the basic distribution $\varphi_j$. In formulae (4) and (5), i denotes the number of a sensor value included in each sensor value distribution, which is an integer from 1 to N. N denotes the number of sensor values measured within a predetermined time during which a sensor value distribution is calculated, and N=100 in the present embodiment. Each of the sensor value distribution represents a distribution of N sensor values. i denotes what number a sensor value is among N sensor values. The sensor value number i may be different from a number in the time serial order of sensor values measured for a behavior. For example, the sensor value number i may be a number in ascending order.

In formula (5), $w_{d,i}$ denotes the ith sensor value included in the dth sensor value distribution $h_d$ stored in the sensor-value distribution database 41. In formula (4), $z_{d,i}$ denotes a value indicating by which basic distribution $w_{d,i}$ is generated. In the first embodiment, the number T of basic distributions and the parameters α and β are included in predetermined estimation conditions determined in advance by a designer of the behavior identification device 1. FIG. 5 shows a graphical model of a generation process assumed in the analysing unit 31 in the behavior identification device 1 according to the present embodiment. In FIG. 5, arrows indicate which data is generated by which data, and T, N, and D denote the number of times that data is generated.

The shape of each sensor value distribution approximates the shape of a mixture distribution of T basic distributions $\varphi_j$ estimated by the analysing unit 31 and in the dth sensor value distribution, the mixing ratio of the basic distribution $\varphi_j$ is the component ratio $\theta_{d,j}$. The sensor value distribution $h_d$ can thus be ideally represented by the following formula (6). From a different point of view, assuming that the sensor value distribution $h_d$ is a vector including the frequency of occurrence of each sensor value as its element, T basic distributions $\varphi_j$ are basis vectors, and the sensor value distribution is approximated by multiplying a linear sum of T basic distributions $\varphi_j$, whose coefficient is the component ratio $\theta_{d,j}$, by a proportional coefficient. The proportional coefficient is the number N of sensor values constituting the sensor value distribution $h_d$. That is, T basic distributions $\varphi_j$ estimated by the analysing unit 31 are components constituting the sensor value distribution $h_d$ stored in the sensor-value distribution database 41. Additionally, the component ratio $\theta_{d,j}$ estimated by the analysing unit 31 indicates the constituent ratio (the mixing ratio) of the components. Assuming that the sensor value distribution $h_d$ and the basic distribution $\varphi_j$ are vectors, V, which indicates the number of classes (bins) of a histogram, denotes the number of dimensions of a vector.

[Formula 6]

$$h_d \propto \sum_{j=1}^{T} (\theta_{d,j} \times \phi_j) \tag{6}$$

In a behavior such as "stopping", "walking", or "running", a component behavior constituting the behavior is regarded as an operation of each part of a body. However, it is difficult to specifically define in advance such an operation of each part of a body as the component behavior and to configure an identification device for each component behavior. In contrast, the behavior identification device 1 according to the present embodiment obtains a sensor value distribution in advance for each of various behaviors and calculates the basis for a set of obtained sensor value distributions. In this way, a component constituting a behavior can be calculated without being defined by a designer.

The basic distribution $\varphi_j$ and the component ratio $\theta_{d,j}$ can be estimated based on an LDA generation process by a repetitive process such as variational Bayes or Gibbs sampling (for example, David M. Blei, Andrew Y. Ng, and Michael I. Jordan, "Latent Dirichlet allocation", Journal of Machine Learning Research, vol. 3, pp. 993-1022, 2003, and Thomas L. Griffiths and Mark Steyvers, "Finding scientific topics", in Proceedings of the National Academy of Sciences of the United States of America, vol. 101, pp. 5228-5235, 2004). Detailed descriptions of these processes are omitted.

The parameters α and β can be automatically estimated by Minka's fixed-point iteration (Thomas P. Minka, "Estimating a Dirichlet distribution", Technical report, Massachusetts Institute of Technology, vol. 2000, pp. 1-13, 2000.). The analysing unit 31 operates as described above.

Next, the evaluating unit 32 is described. The evaluating unit 32 evaluates a basic distribution and a component ratio that are estimated by the analysing unit 31. If an evaluation result does not satisfy predetermined evaluation criteria, the analysing unit 31 changes predetermined estimation conditions and then estimates again the basic distribution and the component ratio. In the present embodiment, for a set of sensor value distributions stored in the sensor-value distribution database 41, the evaluating unit 32 calculates an average of component ratios $\theta_{d,j}$ for each basic distribution $\varphi_j$, and sets the calculated average as the evaluation criteria. FIGS. 6A and 6B are diagrams for explaining an operation of the evaluating unit 32 in the behavior identification device 1 according to the present embodiment. In FIGS. 6A and 6B, the horizontal axis indicates a basic distribution number j and the vertical axis indicates a component ratio. FIG. 6A shows an example of a set $\theta_d$ of component ratios estimated by the analysing unit 31 for each sensor value distribution. The set $\theta_d$ of component ratios is constituted by the component ratio $\theta_{d,j}$ of each basic distribution in each sensor value distribution. The evaluating unit 32 calculates first an average component ratio $\theta a_j$, which is an average of the component ratios $\theta_{d,j}$ for each basic distribution by the following formula (7).

[Formula 7]

$$\theta a_j = \left( \sum_{d=1}^{D} \theta_{d,j} \right) / D \tag{7}$$

FIG. 6B shows an example of θa, which is a set of calculated average component ratios $\theta a_j$. The average component ratio indicates in what ratio each basic distribution is included, on average, in a set of sensor value distributions stored in the sensor-value distribution database 41. A basic distribution having an extremely small average component ratio is hardly included in sensor value distributions stored in the sensor-value distribution database 41. That is, the number T of basic distributions set in advance might be too large. To perform such an evaluation, the evaluating unit 32 compares each average component ratio $\theta a_j$ to a predetermined threshold th.

If all the average component ratios $\theta a_j$ are larger than or equal to the threshold th, the evaluating unit 32 stores a basic distribution in the component database 42 and a component ratio in the component ratio database 43. On the other hand, if one of the average component ratios θa_j is less than the threshold th, the evaluating unit 32 subtracts the number T of basic distributions set in advance by 1. The analysing unit 31 then estimates again a basic distribution and a component ratio based on a set of sensor value distributions stored in the sensor-value distribution database 41 by using the updated number T of basic distributions as a new condition. According to the example of FIG. 6B, in a set θa of average component ratios, a ratio θa_4 of the fourth basic distribution is less than the threshold th. Consequently, the analysing unit 31 estimates again a basic distribution and a component ratio under conditions that the number T of basic distributions is subtracted by 1.

Figure 7:
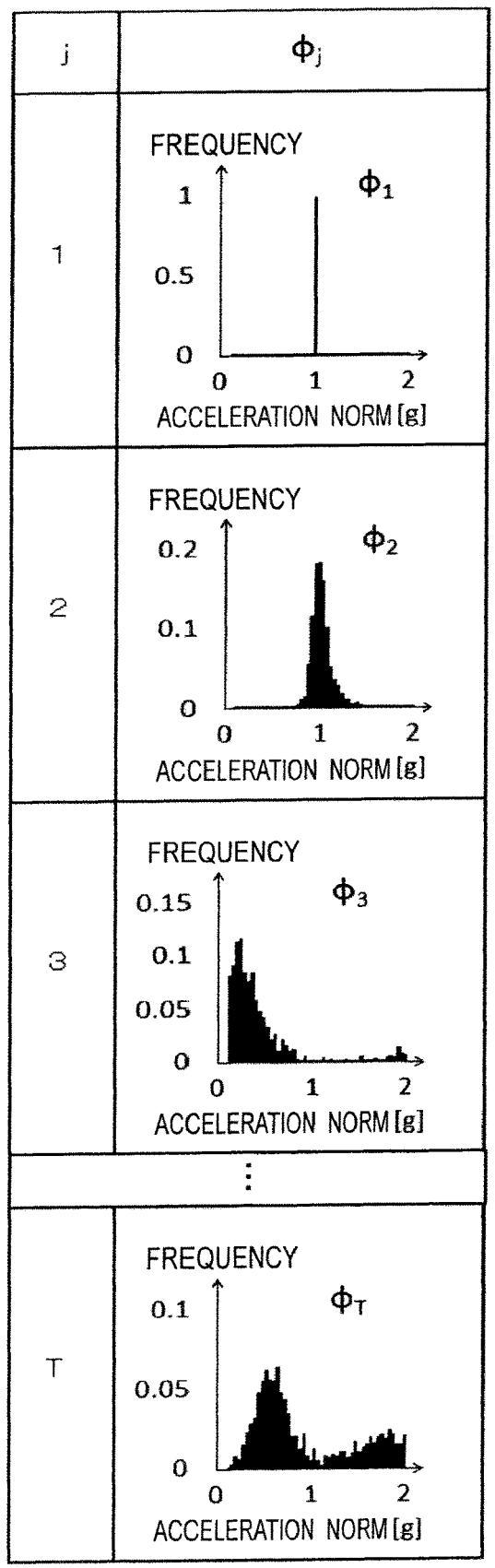
FIG. 7 is a diagram for explaining a data structure of a component database in the behavior identification device according to the first embodiment of the present invention.

The evaluation criteria of the evaluating unit 32 is not limited to the criteria described above. Alternatively, a sensor value distribution may be reproduced using a basic distribution and a component ratio that are estimated by the analysing unit 31, the reproduced sensor value distribution may be compared to a sensor value distribution stored in the sensor-value distribution database 41, and differences between these sensor value distributions may be used as the evaluation criteria. The evaluating unit 32 operates as described above. Next, the component database 42 is described. The component database 42 stores therein a basic distribution φ_j calculated by the basic distribution generating unit 30. FIG. 7 is a diagram for explaining a data structure of the component database 42 in the behavior identification device 1 according to the present embodiment. The component database 42 stores therein the basic distribution φ_j in association with the basic distribution number j.

Next, the component ratio database 43 and the input unit 4 are described. The component ratio database 43 stores therein a set θ_d of component ratios calculated by the basic distribution generating unit 30 for each sensor value distribution. In addition, the component ratio database 43 stores therein a behavior label of a target when each sensor value distribution is measured in association with a component ratio. FIG. 8 is a diagram for explaining a data structure of the component ratio database 43 in the behavior identification device 1 according to the present embodiment. The component ratio database 43 stores therein a set θ_d of component ratios and a behavior label in association with the data number d of a sensor value distribution. Each component ratio θ_{d,j} constituting the set θ_d of component ratios is stored in association with the basic distribution number j.

In FIG. 8, for a first sensor value distribution stored in the sensor-value distribution database 41, for example, the component ratio database 43 stores therein the behavior label "stopping" together with a set θ_1 of component ratios included in the first sensor value distribution. The behavior label is input by the input unit 4. The input unit 4 is configured by a device that can externally input information, such as a keyboard, a touch panel, or a memory card read device. The behavior identification device 1 according to the present embodiment generates a basic distribution φ_j and a set θ_d of component ratios based on a sensor value distribution calculated for a behavior of a target in a generation phase. However, the operation of the behavior identification device 1 is not limited thereto. For example, the behavior identification device 1 may generate a basic distribution φ_j and a set θ_d of component ratios based on a sensor value distribution calculated in advance for a behavior of a person, who is not a target. The behavior identification device 1 according to the present embodiment operates in the generation phase as described above.

Next, an operation of the behavior identification device 1 in an identification phase is described. The sensor-value obtaining unit 10 is described first. The sensor-value obtaining unit 10 obtains a sensor value from the sensor 2 and calculates a sensor value distribution h2 in the same manner as in the generation phase. The sensor value distribution h2 is a histogram and thus is represented as a set of measurement frequencies of each sensor value. That is, h2={h2(1), h2(2), h2(3), . . . , h2(V)}. h2(v) denotes the measurement frequency of a sensor value corresponding to the vth class in the sensor value distribution h2. Next, the ratio calculating unit 21 is described. For the sensor value distribution h2 calculated in the identification phase, the ratio calculating unit 21 calculates a component ratio θ2_j, which is a ratio of each basic distribution included in the sensor value distribution h2, using the basic distribution φ_j stored in the component database 42. As described above, j denotes a basic distribution number. That is, the component ratio θ2_j indicates a ratio of the jth basic distribution included in the sensor value distribution h2. A set of component ratios in the sensor value distribution h2 is denoted by θ2. That is, θ2={θ2_1, θ2_2, . . . , θ2_T}. Specifically, the ratio calculating unit 21 calculates the set θ2 of component ratios of the basic distribution φ_j included in the sensor value distribution h2 using the EM algorithm. The EM algorithm estimates parameters of a probability model based on the maximum likelihood method.

It is assumed that a sensor value that constitutes the sensor value distribution h2 calculated by the sensor-value obtaining unit 10 is denoted by w2_i. As described above, i denotes the number of a sensor value included in the sensor value distribution h2, which is an integer from 1 to N. The ratio calculating unit 21 performs the following first procedure and then alternately repeats a second procedure and a third procedure for predetermined times based on the EM algorithm. In the first procedure, the ratio calculating unit 21 sets an initial value of the component ratio θ2_j included in a sensor value distribution. Next, in the second procedure, the ratio calculating unit 21 calculates a probability ψ_{i,j} that the ith sensor value w2_i included in the sensor value distribution h2 is generated by the jth basic distribution φ_j using the following formula (8). In formula (8), v2_i indicates which class in a histogram the ith sensor value w2_i belongs to. Next, in the third procedure, the ratio calculating unit 21 calculates the component ratio θ2_j using the following formula (9). The second procedure is referred to as M-step and the third procedure is referred to as E-step. The ratio calculating unit 21 operates as described above.

[Formula 8]
$$\psi_{i,j} = (\theta 2_j \times \phi_j(v2_i)) / \left( \sum_{k=1}^{T} (\theta 2_k \times \phi_k(v2_i)) \right) \quad (8)$$

[Formula 9]
$$\theta 2_j = \left( \sum_{i=1}^{N} \psi_{i,j} \right) / N \quad (9)$$

Next, the identification unit 22 is described. The identification unit 22 calculates the similarity between the set θ2 of component ratios calculated by the ratio calculating unit 21 and a set θ_d of component ratios for each sensor value distribution stored in the component ratio database 43. The identification unit 22 then obtains, as an identification result, a behavior label corresponding to a set of component ratios having the highest similarity among sets $\theta_d$ of component ratios stored in the component ratio database 43. FIGS. 9A, 9B, and 9C are diagrams for explaining an operation of the identification unit 22 in the behavior identification device 1 according to the present embodiment. The operation of the identification unit 22 is specifically described with reference to FIGS. 9A, 9B, and 9C. FIG. 9A shows an example of the set θ2 of component ratios calculated by the ratio calculating unit 21. FIG. 9B shows an example of the set $\theta_d$ of component ratios stored in the component ratio database 43.

The identification unit 22 calculates first the similarity between the set θ2 of component ratios calculated by the ratio calculating unit 21 and the set $\theta_d$ of component ratios for each sensor value distribution stored in the component ratio database 43. The identification unit 22 calculates the similarity between component ratios using Histogram Intersection. Histogram Intersection is an index indicating the similarity between two histograms, and becomes larger as the similarity becomes higher. Additionally, Histogram Intersection has a maximum value of 1 and a minimum value of 0. The identification unit 22 calculates D similarities $HI_d$ by formula (10). In formula (10), min(A1, A2) means a calculation of the minimum value of A1 and A2. FIG. 9C shows an example of a calculated similarity $HI_d$.

[Formula 10]

$$HI_d = \sum_{j=1}^{T} \min(\theta_{d,j}, \theta 2_j) \quad (10)$$

As described above, the component ratio database 43 stores therein a set $\theta_d$ of component ratios and a behavior label in association with a sensor value distribution number d. The identification unit 22 searches for a component ratio having the highest similarity $HI_d$ to the set θ2 of component ratios among D sets $\theta_d$ of component ratios stored in the component ratio database 43. The identification unit 22 then outputs a behavior label corresponding to the searched set of component ratios as an identification result. In the example shown in FIG. 9C, the similarity to the second set $\theta_2$ of component ratios stored in the component ratio database 43 is 0.959, which is the maximum value, and thus the identification unit 22 identifies the label "walking" corresponding to the second set $\theta_2$ of component ratios. The identification unit 22 outputs the identification result to the display unit 3 that is externally provided to the behavior identification device 1. The display unit 3 is an image device that displays identification results, such as a liquid crystal display. Instead of the display unit 3, a storage device that stores therein identification results or a communication device that transmits identification results may be provided. The behavior identification device 1 according to the present embodiment operates as described above.

Figure 10:
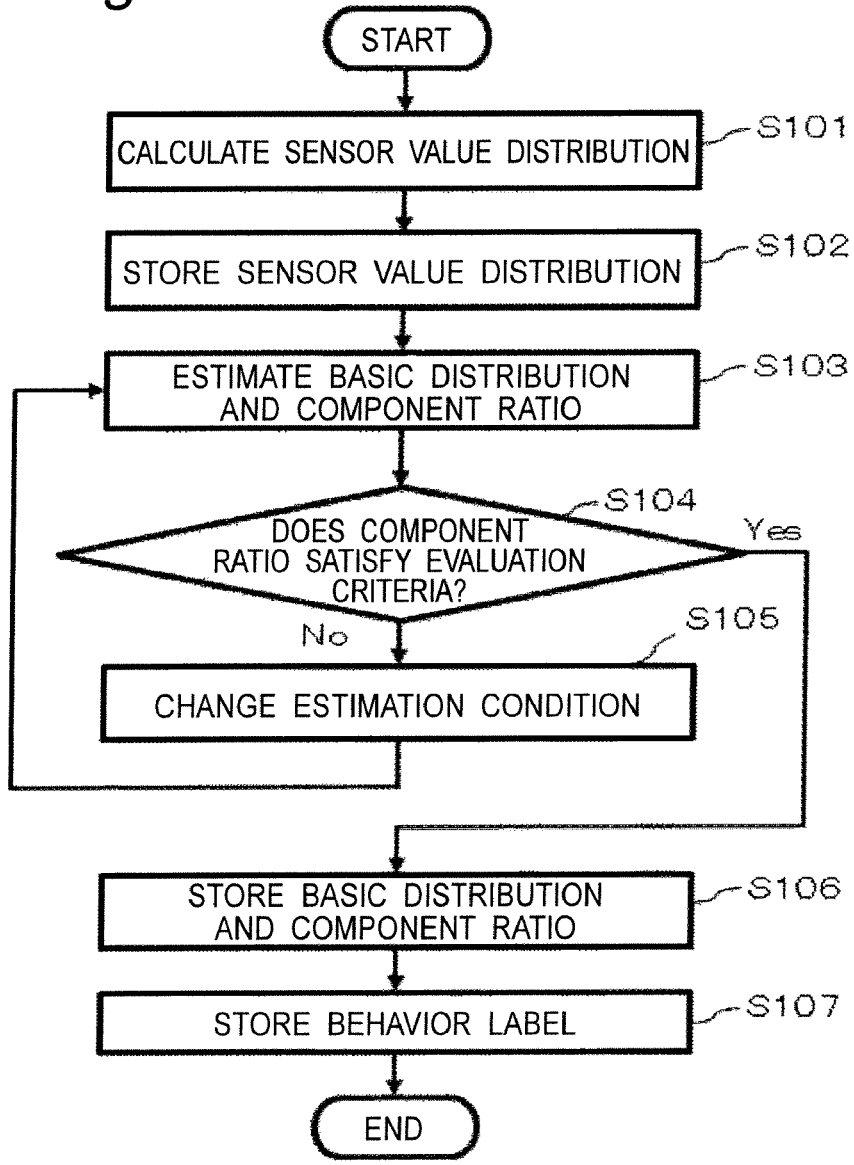
FIG. 10 is a flowchart of an operation of the behavior identification device according to the first embodiment of the present invention in a generation phase.

The operation of the behavior identification device 1 according to the present embodiment is further described with reference to a flowchart. The behavior identification device 1 operates in a generation phase in advance and then operates in an identification phase. If the behavior identification device 1 has already operated in the generation phase, the behavior identification device 1 may successively operate in the identification phase. An operation of the behavior identification device 1 in the generation phase is described first. FIG. 10 is a flowchart of the operation of the behavior identification device 1 according to the present embodiment in the generation phase. In the generation phase, the sensor-value obtaining unit 10 obtains first a sensor value from the sensor 2 and calculates a sensor value distribution (Step S101). Next, the sensor-value distribution database 41 stores therein the sensor value distribution calculated at Step S101 (Step S102).

Next, the analysing unit 31 estimates a basic distribution that is a component constituting a sensor value distribution and a component ratio that is a ratio of each basic distribution included in a sensor value distribution (Step S103). At Step S103, the analysing unit 31 estimates a basic distribution and a component ratio based on the sensor value distribution stored at Step S102. Next, the evaluating unit 32 evaluates the basic distribution and the component ratio estimated at Step S103 (Step S104). At Step S104, the evaluating unit 32 determines whether the component ratio calculated for each basic distribution satisfies predetermined evaluation criteria to evaluate the basic distribution and the component ratio. If the component ratio does not satisfy the evaluation criteria, the operation of the behavior identification device 1 proceeds to Step S105. At Step S105, the evaluating unit 32 changes an estimation condition used at Step S103. When Step S105 ends, the operation of the behavior identification device 1 returns to Step S103.

On the other hand, if the component ratio satisfies the evaluation criteria, the operation of the behavior identification device 1 proceeds to Step S106. At Step S106, the component database 42 stores therein the basic distribution in association with a basic distribution number, whereas the component ratio database 43 stores therein the component ratio in association with a data number of the sensor value distribution. At Step S106, the component database 42 stores therein the basic distribution and the component ratio database 43 stores therein the component ratio. Next, the component ratio database 43 stores therein a behavior label of a target when the sensor value distribution is calculated in association with the data number of the sensor value distribution (Step S107). As a result, the component ratio database 43 stores therein the component ratio in association with the behavior label. The behavior identification device 1 may perform the operation at Step S107 at any time after Step S102. When the operation at Step S107 ends, the operation of the behavior identification device 1 in the generation phase ends.

Figure 11:
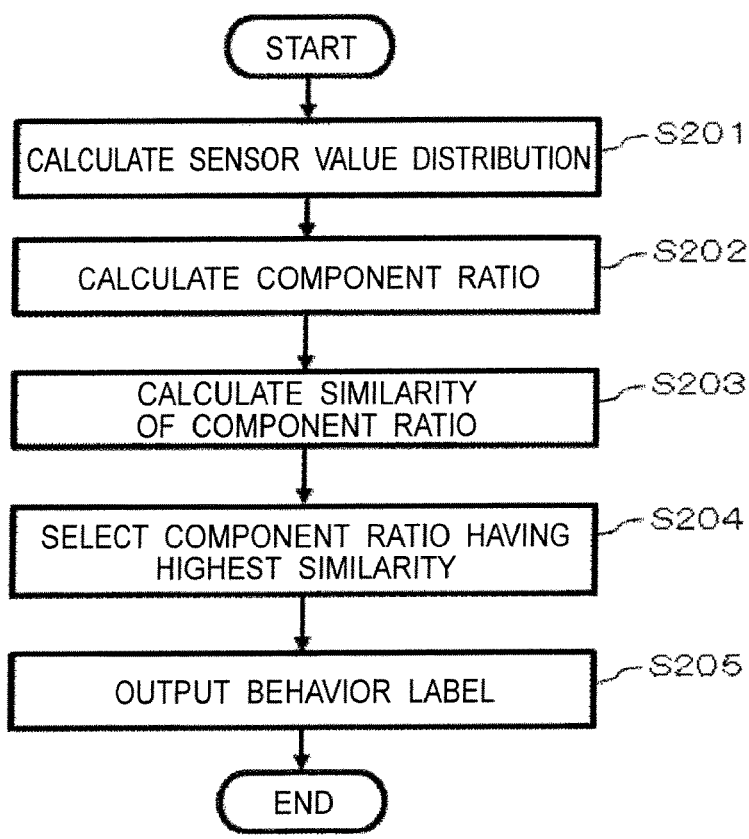
FIG. 11 is a flowchart of an operation of the behavior identification device according to the first embodiment of the present invention in an identification phase.

Next, an operation of the behavior identification device 1 in the identification phase is described. FIG. 11 is a flowchart of the operation of the behavior identification device 1 according to the present embodiment in the identification phase. In the identification phase, the sensor-value obtaining unit 10 obtains first a sensor value from the sensor 2 and calculates a sensor value distribution (Step S201). Next, the ratio calculating unit 21 calculates a component ratio in the sensor value distribution calculated at Step S201 using a basic distribution stored in the component database 42 (Step S202). The component ratio calculated at Step S202 is a ratio of each basic distribution included in the sensor value distribution.

Next, the identification unit 22 calculates the similarity between a set of component ratio calculated at Step S202 and each set of component ratios stored at Step S106 in the generation phase (Step S203). Next, the identification unit 22 selects a set of component ratio having the highest similarity among the sets of component ratios stored at Step S106 in the generation phase (Step S204). The identification unit 22 then outputs a behavior label corresponding to the set of component ratios selected at Step S204 as an identification result (Step S205). When the operation at Step S205 ends, the operation of the behavior identification device 1 in the identification phase ends. The behavior identification device 1 operates as described above.

Next, the hardware configuration that achieves the behavior identification device 1 according to the present embodiment is described. Functions of the sensor-value obtaining unit 10, the ratio calculating unit 21, the identification unit 22, and the basic distribution generating unit 30 in the behavior identification device 1 are achieved by processing circuits. The processing circuit may be dedicated hardware or may be a CPU that executes programs stored in memories (Central Processing Unit, which is also referred to as a processing unit, a computing unit, a microprocessor, a microcomputer, a processor, or a DSP). Additionally, functions of the sensor-value distribution database 41, the component database 42, and the component ratio database 43 are achieved by memories.

When the processing circuit is dedicated hardware, examples of the processing circuit include a single circuit, a composite circuit, a programmed processor, a parallel-programmed processor, an ASIC, an FPGA, and any combination thereof. The functions of the sensor-value obtaining unit 10, the ratio calculating unit 21, the identification unit 22, and the basic distribution generating unit 30 may be achieved by processing circuits, respectively, or may be achieved by a single processing circuit.

When the processing circuit is a CPU, the functions of the sensor-value obtaining unit 10, the ratio calculating unit 21, the identification unit 22, and the basic distribution generating unit 30 are achieved by software, firmware, or a combination of software and firmware. The software and the firmware are described as programs and stored in memories. The processing circuit achieves the functions of units by reading the programs stored in the memories and executing the programs. These programs are for causing a computer to perform procedures or methods of operating the sensor-value obtaining unit 10, the ratio calculating unit 21, the identification unit 22, and the basic distribution generating unit 30. Examples of the memory include a non-volatile or volatile semiconductor memory such as a RAM, a ROM, a flash memory, an EPROM, and an EEPROM, a magnetic disk, a flexible disk, an optical disk, a compact disk, a mini disk, and a DVD.

A part of the functions of the sensor-value obtaining unit 10, the ratio calculating unit 21, the identification unit 22, and the basic distribution generating unit 30 may be achieved by dedicated hardware and another part thereof may be achieved by software or firmware. For example, a processing circuit, which is dedicated hardware, may achieve the function of the sensor-value obtaining unit 10, and a processing circuit may achieve the functions of the ratio calculating unit 21, the identification unit 22, and the basic distribution generating unit 30 by reading programs stored in memories and executing the programs.

Figure 12:
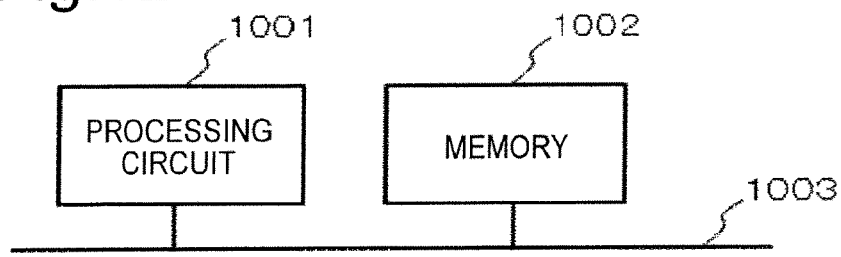
FIG. 12 shows an example of a hardware configuration of the behavior identification device according to the first embodiment of the present invention.

FIG. 12 shows an example of the hardware configuration of the behavior identification device 1 according to the present embodiment. FIG. 12 shows an example in a case where a processing circuit 1001 is dedicated hardware. In the example of FIG. 12, the processing circuit 1001 achieves functions of the sensor-value obtaining unit 10, the ratio calculating unit 21, the identification unit 22, and the basic distribution generating unit 30. A memory 1002 achieves functions of the sensor-value distribution database 41, the component database 42, and the component ratio database 43. The processing circuit 1001 is connected via a data bus 1003 to the memory 1002.

Figure 13:
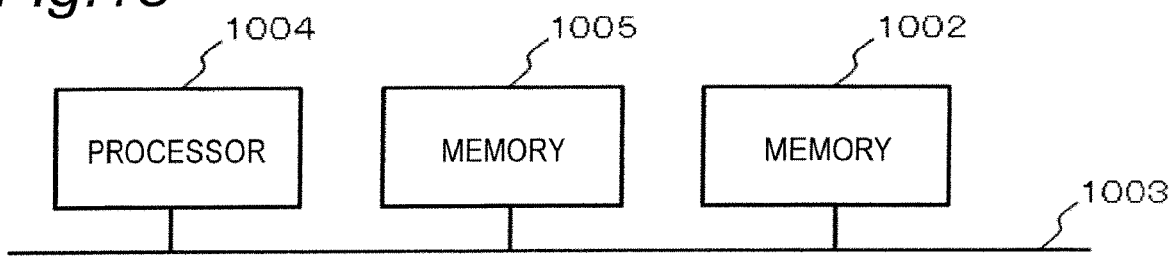
FIG. 13 shows another example of the hardware configuration of the behavior identification device according to the first embodiment of the present invention.

FIG. 13 shows another example of the hardware configuration of the behavior identification device 1 according to the present embodiment. FIG. 13 shows an example of the hardware configuration in a case where a processing circuit is a CPU. In the example of FIG. 13, functions of the sensor-value obtaining unit 10, the ratio calculating unit 21, the identification unit 22, and the basic distribution generating unit 30 are achieved by a processor 1004 executing programs stored in a memory 1005. Functions of the sensor-value distribution database 41, the component database 42, and the component ratio database 43 are achieved by the memory 1002. The processor 1004 is connected via the data bus 1003 to the memory 1002 and the memory 1005. Behavior identification devices according to subsequent embodiments can be achieved by the same hardware configuration as in the behavior identification device 1 according to the present embodiment.

As described above, the behavior identification device 1 according to the present embodiment can calculate a basic distribution constituting a sensor value distribution based on a sensor value distribution obtained for a behavior such as "stopping", "walking", or "running". Consequently, it is possible to identify a behavior more flexibly as a combination of component constituting the behavior without defining components constituting the behavior by a designer.

In addition, the behavior identification device 1 according to the present embodiment can identify more flexibly even a behavior that cannot be specifically defined by a designer as a combination of components constituting the behavior. For example, it is difficult for a designer to define a component constituting a behavior that is vaguely defined by the designer, such as "behavior indicating that a person seems to be in a hurry". That is to say, the behavior that is vaguely defined is a behavior that is defined conceptually. However, the behavior identification device according to the first embodiment can identify the behavior that is vaguely defined if a behavior label stored in the component ratio database 43 is associated with the behavior that is vaguely defined.

While "behavior" collectively means the behavior, action, and posture of a target and the like in the present embodiment, the behavior is not limited thereto. The present invention can also be applied to an operation of a target other than a human being (for example, an action of an animal or an operation of a machine with unknown control contents). For the operation of a target other than a human being, in most cases, it is difficult for a designer of a behavior identification device to define a component constituting a behavior, and thus it is effective to apply the present invention to such a case.

Second Embodiment

There are some modes in a behavior in a target's daily life. The mode collectively means a scene that affects a behavior of a target, a physical state, and the like. That is to say, the mode is a condition that affects a behavior of a target. The mode is thus a clue for identifying a behavior of a target. Examples of the mode include "at home", "in factory", "in park", "good physical condition", and "bad physical condition". If the mode of a behavior of a target differs, it is thought that a set of basic distributions constituting a sensor value distribution differs. For example, even in the same behavior "walking", the mode "at home" and the mode "in factory" have different sets of basic distributions constituting a sensor value distribution.

Figure 14:
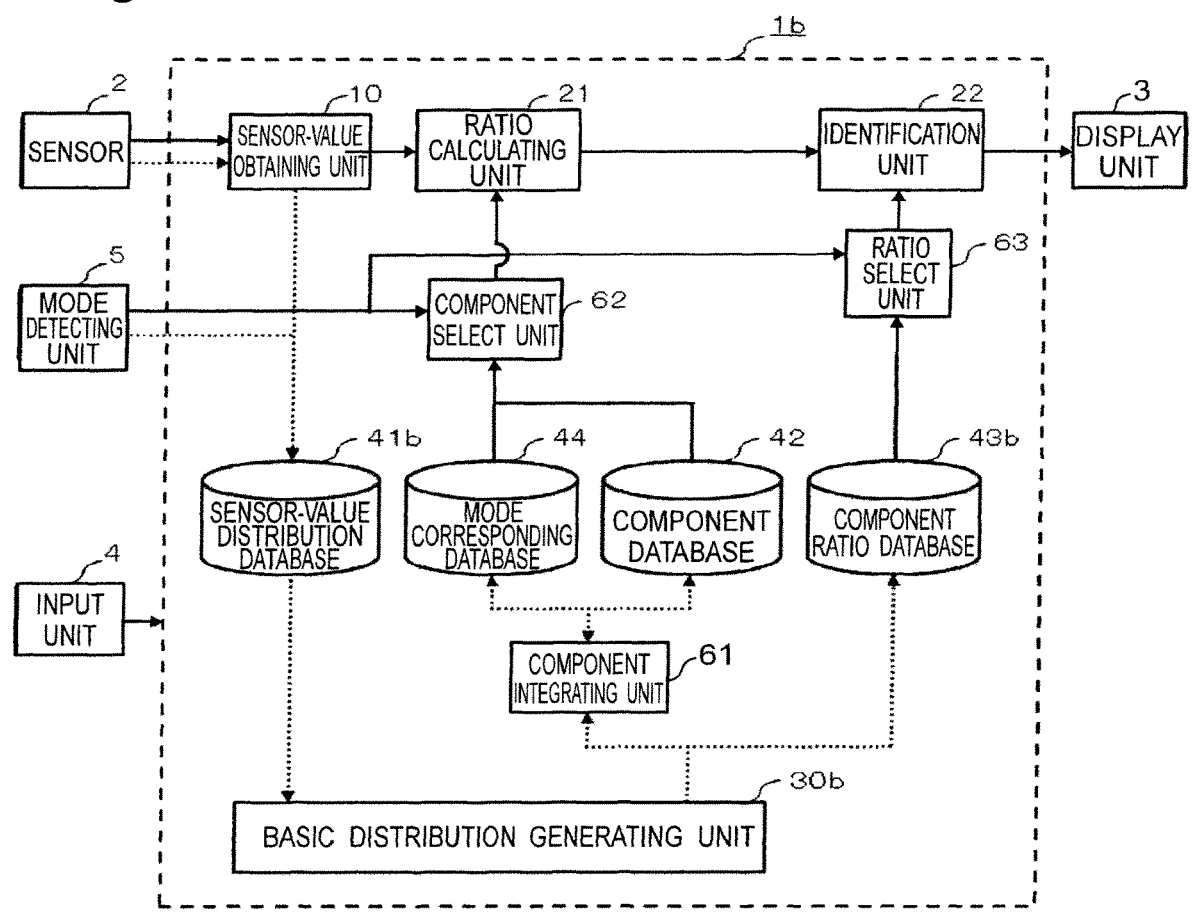
FIG. 14 shows an example of a configuration of a behavior identification device according to a second embodiment of the present invention.

FIG. 14 shows an example of a configuration of a behavior identification device 1b according to a second embodiment of the present invention. The behavior identification device 1b according to the present embodiment is different from the behavior identification device 1 according to the first embodiment in that the behavior identification device 1b detects the mode of a target to calculate a set of basic distributions that is appropriate for each mode. As a result, the behavior identification device 1b according to the present embodiment can achieve behavior identification with higher accuracy. The difference between the behavior identification device 1b according to the present embodiment and the behavior identification device 1 according to the first embodiment is mainly described below.

Similarly to FIG. 1, in FIG. 14, broken line arrows indicate the relationships between blocks in a generation phase, whereas solid line arrows indicate the relationships between the blocks in an identification phase. Comparing to the behavior identification device 1 according to the first embodiment, the behavior identification device 1b according to the present embodiment newly includes a mode corresponding database 44, a component integrating unit 61, a component select unit 62, and a ratio select unit 63. The behavior identification device 1b according to the present embodiment is different from the behavior identification device 1 according to the first embodiment in a part of an operation of a basic distribution generating unit 30b. In addition, the data structure of a sensor-value distribution database 41b and a component ratio database 43b in the behavior identification device 1b according to the present embodiment is different from that in the behavior identification device 1 according to the first embodiment. A mode detecting unit 5 is connected to the behavior identification device 1b.

The mode detecting unit 5 is described first. In the present embodiment, the mode detecting unit 5 detects a mode of a target. The mode detecting unit 5 detects, as a mode, a place where the target is present such as "at home" or "in factory". The mode detecting unit 5 is configured by, for example, a device that is capable of detecting an absolute position on the earth such as GPS (Global Positioning System), a positioning system in which radio waves from a transmitter are received by a plurality of receivers and a position is detected using the radio wave arrival time, the intensity of an electric field, and the like, or a distance measuring system in which the distance from a transmitter is estimated by receiving radio waves from the transmitter. As another example, the mode detecting unit 5 may obtain physical information such as heart rates, body temperature, brain waves, or blood oxygen saturation levels to detect, as the mode of a target, "good physical condition" and "bad physical condition". As yet another example, the mode detecting unit 5 may receive a vertical acceleration value measured by the sensor 2 as an input and detect, as a mode, the posture of a target such as "lying" and "standing".

Figure 15:
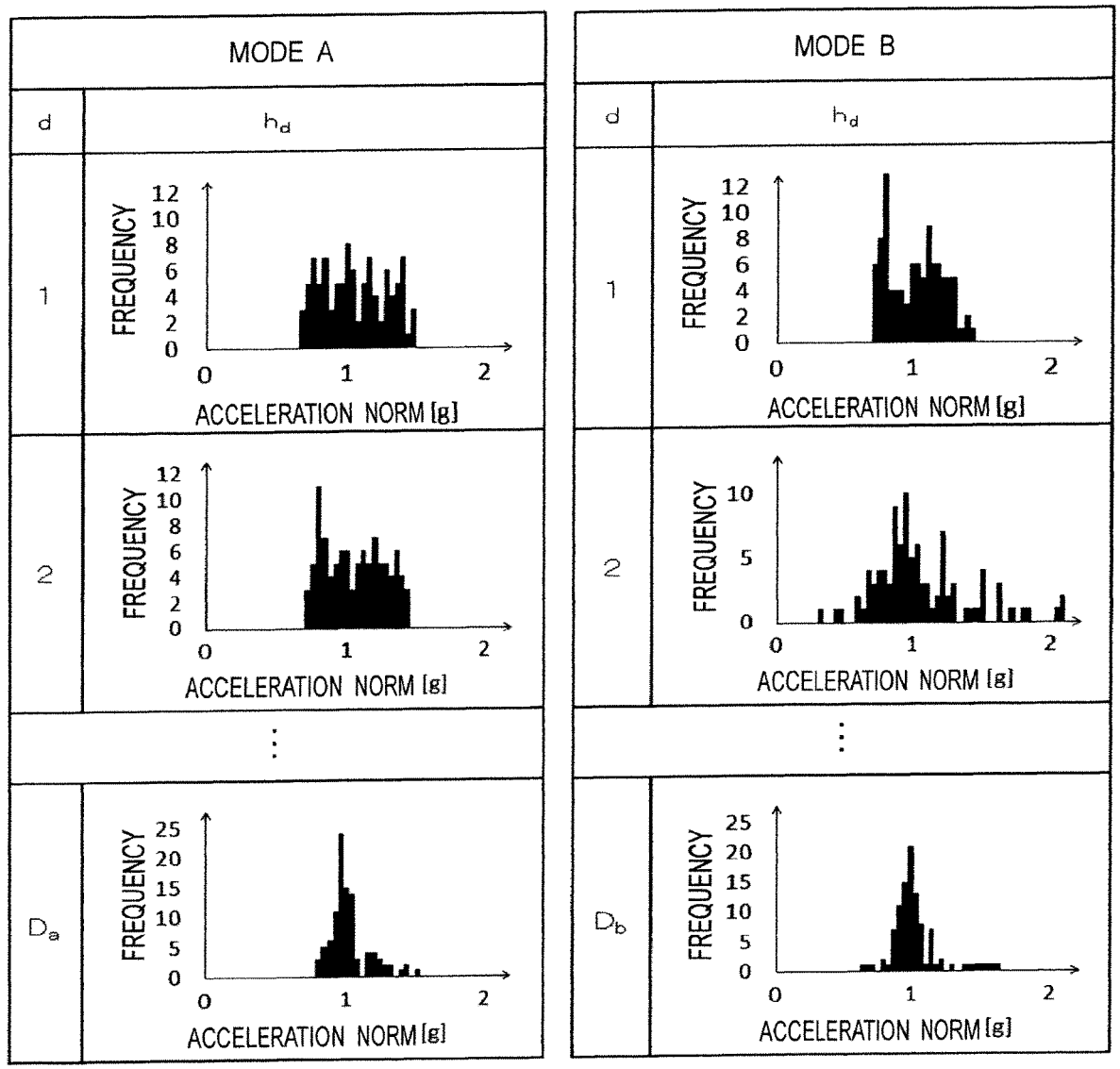
FIG. 15 is a diagram for explaining a data structure of a sensor-value distribution database in the behavior identification device according to the second embodiment of the present invention.

Next, the behavior identification device 1b according to the present embodiment is described. The sensor-value distribution database 41b is described first. The sensor-value distribution database 41b stores therein a set of sensor value distributions calculated by a sensor-value obtaining unit 10 in a generation mode for each mode of a target detected by the mode detecting unit 5. FIG. 15 is a diagram for explaining a data structure of the sensor-value distribution database 41b in the behavior identification device 1b according to the present embodiment. In the behavior identification device 1b according to the present embodiment, a mode A is an "at home" mode and a mode B is an "in factory" mode. In the example of FIG. 15, the sensor-value distribution database 41b stores therein a set of Da sensor value distributions $h_d$ for a mode A and a set of Db sensor value distributions $h_d$ for a mode B.

Next, the basic distribution generating unit 30b is described. The basic distribution generating unit 30b calculates a basic distribution and a component ratio for each mode based on a set of sensor value distributions stored for each mode. Except that the basic distribution and the component ratio are calculated for each mode, the basic distribution generating unit 30b operates in the same manner as in the behavior identification device 1 according to the first embodiment. Next, the component integrating unit 61 is described. The component integrating unit 61 successively selects a basic distribution of each mode from basic distributions calculated for different modes and generates a combination of basic distributions. The component integrating unit 61 compares combined basic distributions in all combinations, determines that basic distributions satisfying a predetermined comparison condition are identical, and integrates these basic distributions. An operation of the component integrating unit 61 is specifically described with reference to the drawings.

Figure 16:
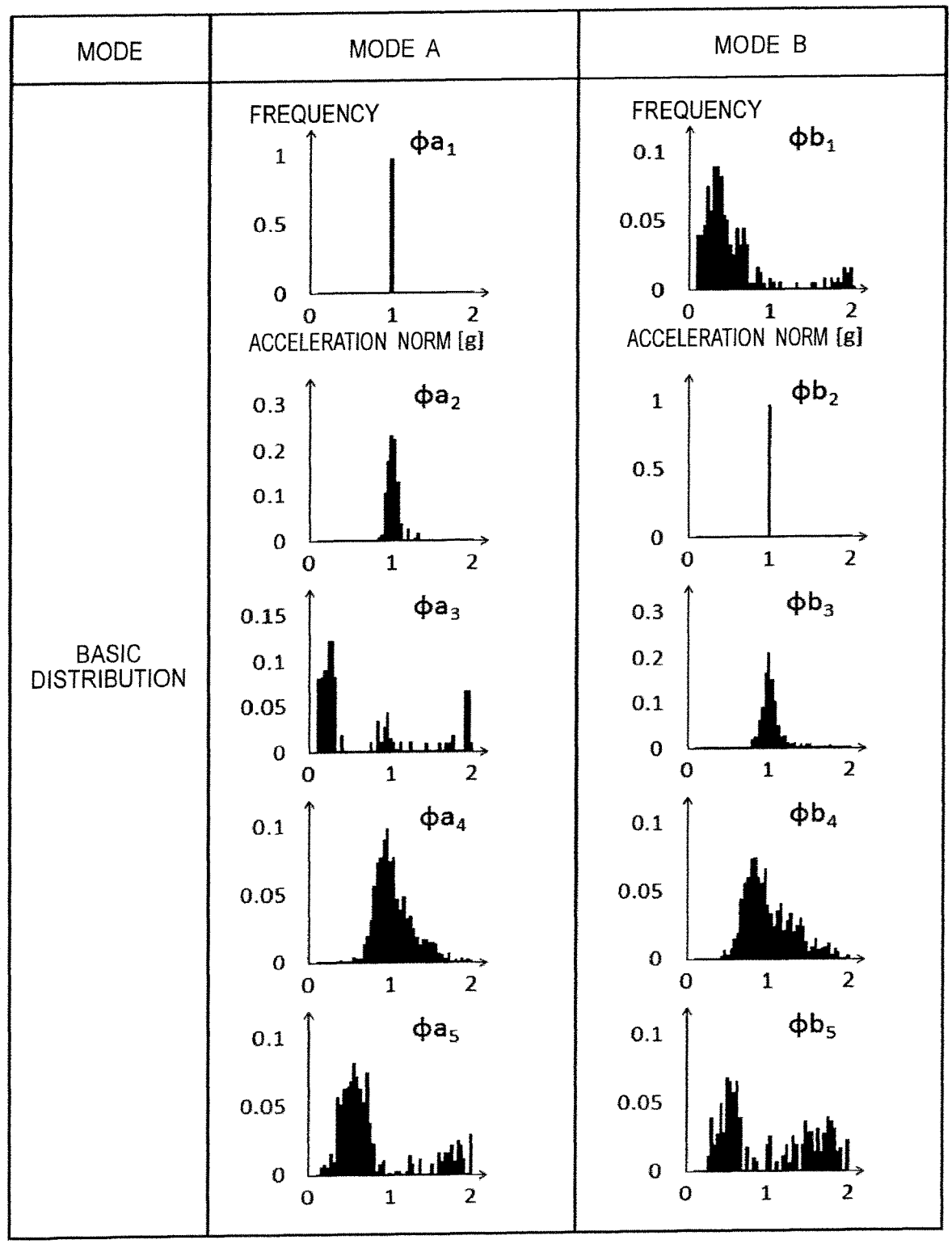
FIG. 16 shows an example of a basic distribution calculated by a basic distribution generating unit in the behavior identification device according to the second embodiment of the present invention.

FIG. 16 shows an example of a basic distribution calculated by the basic distribution generating unit 30b in the behavior identification device 1b according to the present embodiment. The basic distribution generating unit 30b calculates five basic distribution $\varphi a_1$, $\varphi a_2$, $\varphi a_3$, $\varphi a_4$, and $\varphi a_5$ in the mode A, and five basic distribution $\varphi b_1$, $\varphi b_2$, $\varphi b_3$, $\varphi b_4$, and $\varphi b_5$ in the mode B. While the number of basic distributions calculated in the mode A is equal to the number of basic distributions calculated in the mode B in the example of FIG. 16, these numbers do not always need to be equal to each other. The component integrating unit 61 successively combines one of the basic distributions calculated in the mode A with one of the basic distributions calculated in the mode B. In addition, the component integrating unit 61 compares combined basic distributions in all the combinations. The component integrating unit 61 compares basic distributions by using the similarity employing Histogram Intersection as an index.

Figures 17, 18:
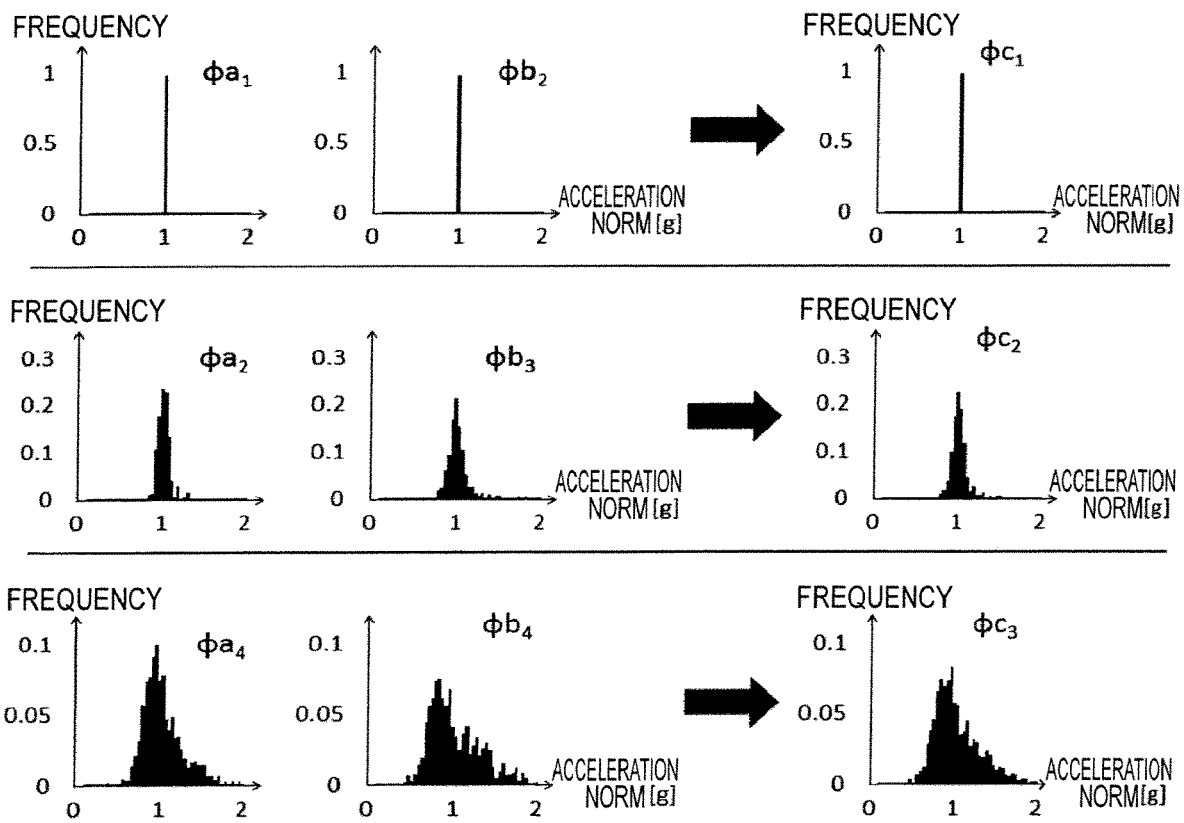
FIG. 17 shows an example of similarity calculated by a component integrating unit in the behavior identification device according to the second embodiment of the present invention.
FIG. 18 is a diagram for explaining an operation of the component integrating unit in the behavior identification device according to the second embodiment of the present invention.

FIG. 17 shows an example of similarity calculated by the component integrating unit 61 in the behavior identification device 1b according to the present embodiment. FIG. 17 shows the similarity between basic distributions shown in FIG. 16, which is calculated by the component integrating unit 61. When the calculated similarity exceeds 0.7, the component integrating unit 61 determines that combined basic distributions are identical and integrates these basic distributions. FIG. 18 is a diagram for explaining an operation of the component integrating unit 61 in the behavior identification device 1b according to the present embodiment. In FIG. 17, since the basic distribution pair with similarity exceeding 0.7 is a $\varphi a_1$ and $\varphi b_2$ pair, a $\varphi a_2$ and $\varphi b_3$ pair, and a $\varphi a_4$ and $\varphi b_4$ pair, the component integrating unit 61 integrates basic distributions of each pair, so that new basic distributions $\varphi c_1$, $\varphi c_2$, and $\varphi c_3$ are obtained.

The component integrating unit 61 integrates basic distributions by averaging frequencies in the same class. When assuming that the basic distribution is a vector, the component integrating unit 61 integrates basic distributions by averaging elements of vectors. When basic distributions combined by the component integrating unit 61 are denoted by $\varphi p$ and $\varphi q$, an integrated basic distribution $\varphi r$ is represented by the following formula (11). In formula (11), $\varphi p(v)$ denotes the frequency of a sensor value corresponding to the vth class in the basic distribution $\varphi p$. $\varphi q(v)$ denotes the frequency of a sensor value corresponding to the vth class in the basic distribution φq. φr(v) denotes the frequency of a sensor value corresponding to the vth class in the basic distribution φr.

[Formula 11]

$$\phi_r(v) = (\phi_p(v) + \phi_q(v))/2 \tag{11}$$

Next, the mode corresponding database 44 is described. The mode corresponding database 44 stores therein a basic distribution corresponding to each mode. FIG. 19 is a diagram for explaining a data structure of the mode corresponding database 44 in the behavior identification device 1b according to the present embodiment. The mode corresponding database 44 stores therein, for each mode, a basic distribution number j used for each mode and information for identifying a basic distribution corresponding to a basic distribution number j among basic distributions stored in the component database 42. For example, the mode corresponding database 44 uses a distribution name as the information for identifying a basic distribution. The component database 42 stores therein a basic distribution that is not integrated by the component integrating unit 61 and a basic distribution obtained by integration. FIG. 20 is a diagram for explaining a data structure of the component database 42 in the behavior identification device 1b according to the present embodiment. The component database 42 stores therein a basic distribution in association with a distribution name.

Next, the component ratio database 43b is described. The component ratio database 43b stores therein a set $\theta_d$ of component ratios calculated by the basic distribution generating unit 30b for each mode. In addition, the component ratio database 43b stores therein a behavior label of a target when a sensor value distribution stored in the sensor-value distribution database 41b is calculated in association with a set of component ratios. FIG. 21 is a diagram for explaining a data structure of the component ratio database 43b in the behavior identification device 1b according to the present embodiment. The component ratio database 43b stores therein, for each mode, a set $\theta_d$ of component ratios and a behavior label in association with a data number d of a sensor value distribution. Each component ratio $\theta_{d,j}$ constituting the set $\theta_d$ of component ratios is stored in association with the basic distribution number j.

Next, the component select unit 62 and the ratio select unit 63 are described. The component select unit 62 refers to the mode corresponding database 44 to select a basic distribution corresponding to a mode of a target detected by the mode detecting unit 5 from the component database 42 and outputs the basic distribution to the ratio calculating unit 21. For example, when the mode B of a target is detected by the mode detecting unit 5, the selection unit 62 refers to the mode corresponding database 44 to select basic distributions $\varphi b_1, \varphi c_1, \varphi c_2, \varphi c_3,$ and $\varphi b_5$ from the component database 42 and outputs these basic distributions to the ratio calculating unit 21. The ratio select unit 63 selects a component ratio corresponding to a mode of a target from the component ratio database 43b and outputs the component ratio to the identification unit 22.

Figure 22:
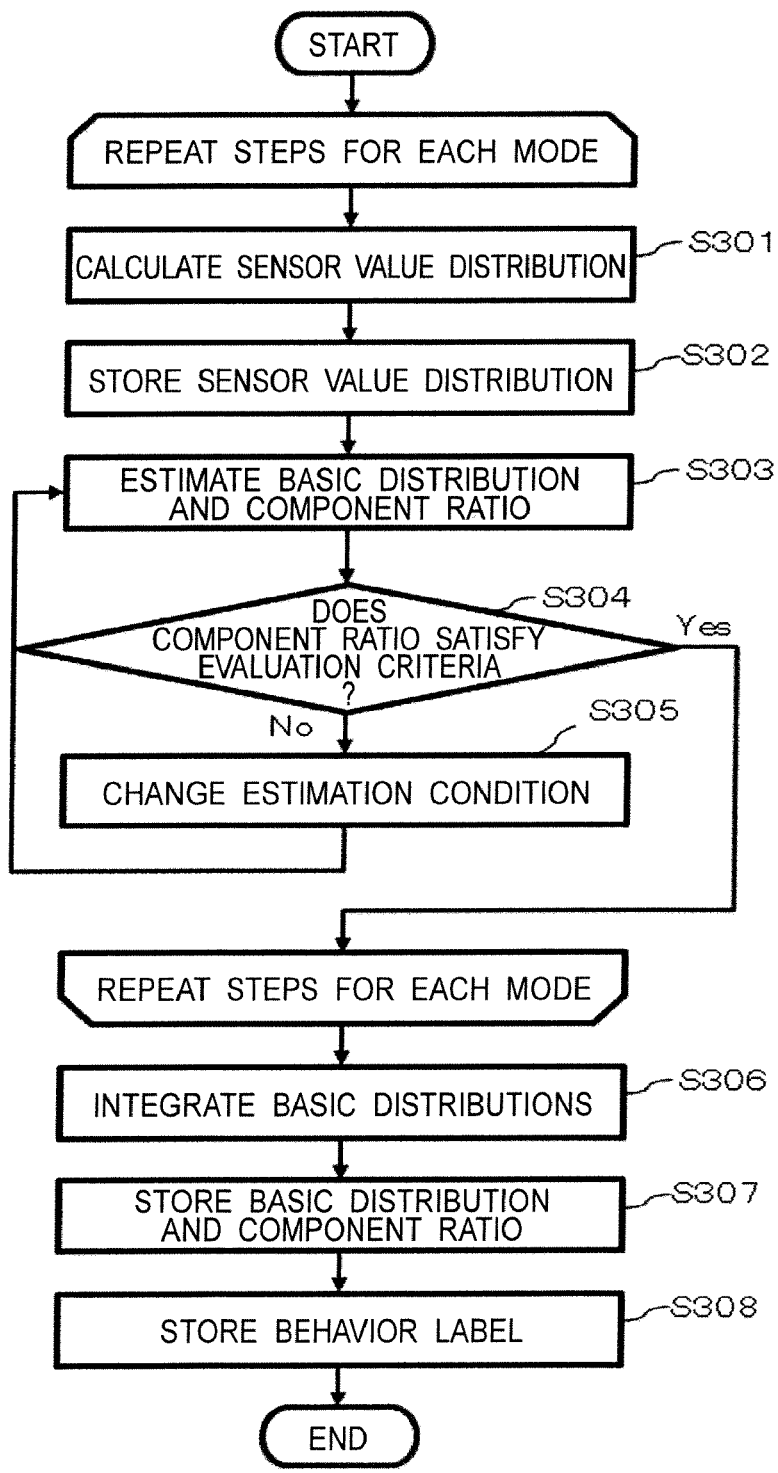
FIG. 22 is a flowchart of an operation of the behavior identification device according to the second embodiment of the present invention in a generation phase.

The operation of the behavior identification device 1b according to the present embodiment is described with reference to a flowchart. The behavior identification device 1b operates in a generation phase in advance and then operates in an identification phase. An operation of the behavior identification device 1b in the generation phase is described first. FIG. 22 is a flowchart of the operation of the behavior identification device 1b according to the present embodiment in the generation phase. In the generation phase, the behavior identification device 1b performs processes from Steps S301 to S305 for each mode detected by the mode detecting unit 5. The sensor-value obtaining unit 10 obtains first a sensor value from the sensor 2 and calculates a sensor value distribution (Step S301). Next, the sensor-value distribution database 41b stores therein the sensor value distribution calculated at Step S301 for each mode (Step S302).

Next, the basic distribution generating unit 30b estimates a basic distribution and a component ratio (Step S303). Next, the basic distribution generating unit 30b evaluates the basic distribution and the component ratio estimated at Step S303 (Step S304). At Step S304, the basic distribution generating unit 30b determines whether the component ratio satisfies predetermined evaluation criteria to evaluate the basic distribution and the component ratio. If the component ratio does not satisfy the evaluation criteria, the operation of the behavior identification device 1b proceeds to Step S305. At Step S305, the basic distribution generating unit 30b changes an estimation condition used at Step S303. When Step S305 ends, the operation of the behavior identification device 1b returns to Step S303. The behavior identification device 1b performs processes from Steps S301 to S305 for each mode.

On the other hand, if the component ratio satisfies the evaluation criteria, the operation of the behavior identification device 1b proceeds to Step S306. At Step S306, the component integrating unit 61 compares basic distributions calculated in different modes, determines that similar basic distributions are identical, and integrates these basic distributions. Next, at step S307, the component database 42 stores therein the basic distribution in association with a basic distribution number, whereas the mode corresponding database 44 stores therein information of the basic distribution used in each mode. Such an operation is thus equivalent to an operation in which the component database 42 stores therein a basic distribution for each mode, and it is possible to reduce required storage capacity. At Step S307, the component ratio database 43b stores therein, for each mode, the component ratio in association with the data number of a sensor value distribution. Next, at Step S308, the component ratio database 43 stores therein a behavior label of a target when the sensor value distribution is calculated in association with the data number of a sensor value distribution. When the operation at Step S308 ends, the operation of the behavior identification device 1 in the generation phase ends.

Figure 23:
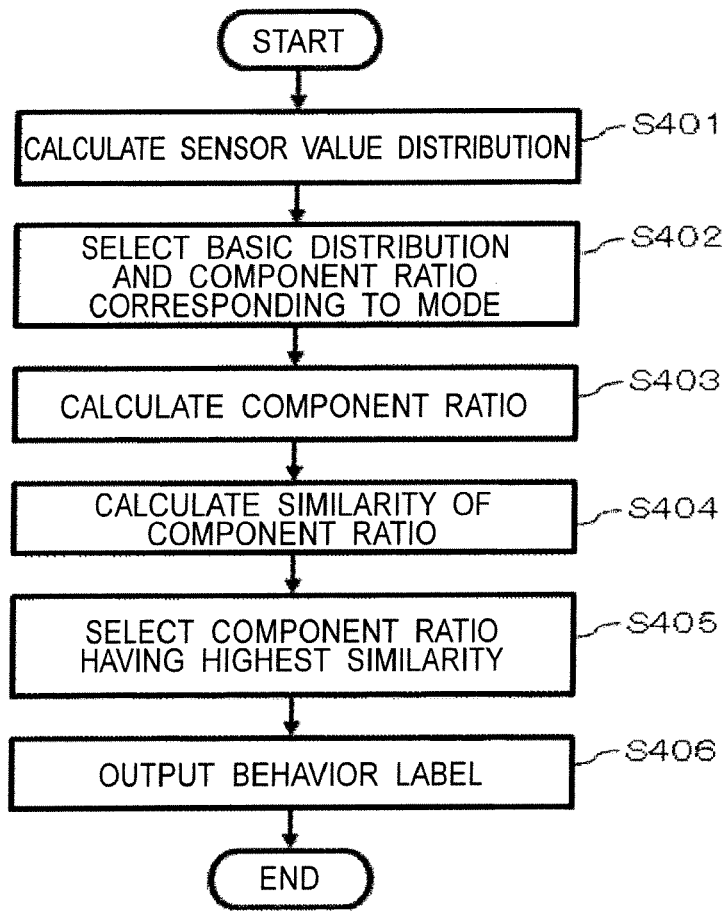
FIG. 23 is a flowchart of an operation of the behavior identification device according to the second embodiment of the present invention in an identification phase.

Next, an operation of the behavior identification device 1b in the identification phase is described. FIG. 23 is a flowchart of the operation of the behavior identification device 1b according to the present embodiment in the identification phase. In the identification phase, the sensor-value obtaining unit 10 obtains first a sensor value from the sensor 2 and calculates a sensor value distribution (Step S401). Next, the component select unit 62 and the ratio select unit 63 select a basic distribution and a component ratio corresponding to a mode detected by the mode detecting unit 5 (Step S402). Next, the ratio calculating unit 21 calculates a component ratio in the sensor value distribution calculated at Step S401 using the basic distribution selected at Step S402 (Step S403).

Next, the identification unit 22 calculates the similarity between a set of component ratios calculated at Step S403 and each set of component ratios stored at Step S307 in the generation phase (Step S404). Next, the identification unit 22 selects a set of component ratio having the highest similarity among the sets of component ratios stored at Step S307 in the generation phase (Step S405). The identification unit 22 then outputs a behavior label corresponding to the set of component ratios selected at Step S405 as an identification result (Step S406). When the operation at Step S406 ends, the operation of the behavior identification device 1b in the identification phase ends. The behavior identification device 1b operates as described above.

The behavior identification device 1b according to the present embodiment detects a mode that affects a behavior of a target such as "at home" or "in factory", selects a set of basic distributions appropriate for each mode, and uses the set of basic distributions. The behavior identification device 1b according to the present embodiment can thus achieve behavior identification with higher accuracy. If the mode of behavior of a target differs, a behavior to be identified by a behavior identification device also differs in most cases. For example, in the "at home" mode, the target is likely to take a behavior such as "lying" or "watching TV". On the other hand, in the "in factory" mode, the target is less likely to take such behaviors.

The behavior identification device 1b according to the present embodiment sets, for each mode of a target, only a label of an appropriate behavior as an identification candidate, and thus achieves behavior identification with higher accuracy. In addition, the behavior identification device 1b according to the present embodiment compares basic distributions calculated in different modes and integrates similar basic distributions, and thus it is possible to prevent excessive use of memories. The behavior identification device 1b according to the present embodiment also has effects identical to those of the behavior identification device 1 according to the first embodiment.

Third Embodiment

The behavior identification device 1 according to the first embodiment identifies a behavior of a target using a sensor value measured by a sensor. It is assumed that the sensor is, for example, a three-axis acceleration sensor that is attached to the waist of the target. In this case, the sensor measures a sensor value that relates to an action of the core of the target's body. The behavior identification device 1 uses a measured sensor value to identify the behavior of the target (for example, "stopping", "walking", or "running"). However, there is no large difference in sensor values measured by the three-axis acceleration sensor attached to the waist of the target between a behavior "going up stairs" and a behavior "climbing ladder". Consequently, the accuracy of identifying a behavior in the behavior identification device 1 may degrade.

Figure 24:
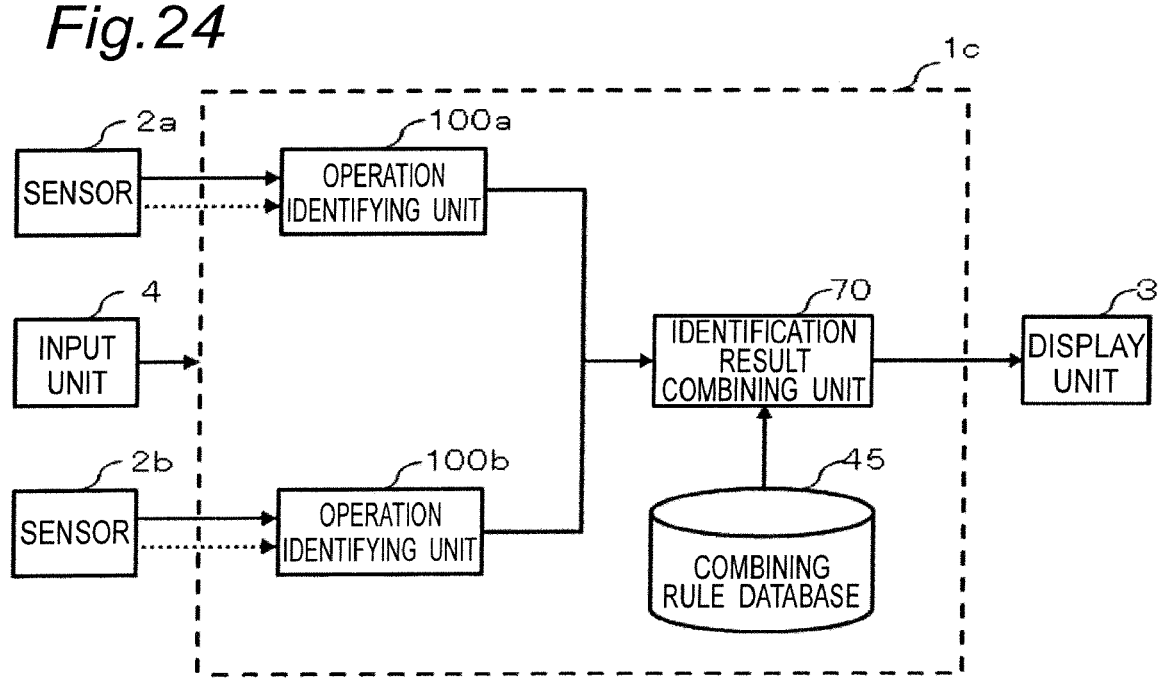
FIG. 24 shows an example of a configuration of a behavior identification device according to a third embodiment of the present invention.

The behavior identification device according to the present embodiment achieves behavior identification with higher accuracy based on sensor values measured by a sensor attached to the wrist of a target, in addition to, for example, a sensor attached to the waist of the target. That is, the behavior identification device according to the present embodiment uses sensor values measured by a plurality of sensors. Differences between the behavior identification device according to the present embodiment and the behavior identification device 1 according to the first embodiment are mainly described below. FIG. 24 shows an example of a configuration of a behavior identification device 1c according to a third embodiment of the present invention. The behavior identification device 1c according to the present embodiment includes operation identifying units 100a and 100b, an identification result combining unit 70, and a combining rule database 45. Similarly to FIG. 1, in FIG. 24, broken line arrows indicate the relationships between blocks in a generation phase, whereas solid line arrows indicate the relationships between the blocks in an identification phase.

FIG. 25 shows an example of a configuration of the operation identifying units 100a and 100b in the behavior identification device 1c according to the present embodiment. The operation identifying units 100a and 100b have an identical configuration to the behavior identification device 1 according to the first embodiment shown in FIG. 1. Similarly to FIG. 1, in FIG. 25, broken line arrows indicate the relationships between blocks in the generation phase, whereas solid line arrows indicate the relationships between the blocks in the identification phase. The operation identifying units 100a and 100b may have an identical configuration to the behavior identification device 1b according to the second embodiment shown in FIG. 14.

As shown in FIG. 24, the operation identifying unit 100a is connected to a sensor 2a and the operation identifying unit 100b is connected to a sensor 2b. The behavior identification device 1c uses sensor values measured by the sensor 2a and the sensor 2b to identify a behavior of a target. The sensor 2a is attached to the waist of the target whereas the sensor 2b is attached to the wrist of the target. The sensor 2a and the sensor 2b are three-axis acceleration sensors that output a sensor value, which is the norm of three-axis acceleration values, every 50 milliseconds. The sensor 2a can measure a sensor value relating to an identification result of a behavior of the core of the target's body (for example, "going up" or "going down"). The sensor 2b can measure a sensor value relating to a behavior of the target's hands (for example, "raising hands", "lowering hands", or "waving hands").

In the generation phase, the operation identifying unit 100a performs an identical process to the behavior identification device 1 according to the first embodiment on a sensor value measured by the sensor 2a. As a result, a basic distribution for the action of the core of the target's body is stored in the operation identifying unit 100a. Next, in the identification phase, the operation identifying unit 100a performs an identical process to the behavior identification device 1 according to the first embodiment on a sensor value measured by the sensor 2a. As a result, the operation identifying unit 100a outputs an identification result of the action of the core of the target's body.

On the other hand, in the generation phase, the operation identifying unit 100b performs an identical process to the behavior identification device 1 according to the first embodiment on a sensor value measured by the sensor 2b. As a result, a basic distribution for the action of the target's hands is stored in the operation identifying unit 100b. Next, in the identification phase, the operation identifying unit 100b performs an identical process to the behavior identification device 1 according to the first embodiment on a sensor value measured by the sensor 2b. As a result, the operation identifying unit 100b outputs an identification result of the action of the target's hands.

In the identification phase, the identification result combining unit 70 combines the identification result of the action of the core of the target's body that is output from the operation identifying unit 100a with the identification result of the action of the target's hands that is output from the operation identifying unit 100b, identifies the behavior of the target, and outputs an identification result. The combining rule database 45 stores therein rules for combining an identification result of an action of the core of the body with an identification result of an action of hands. FIG. 26 is a diagram for explaining a data structure of the combining rule database 45 in the behavior identification device 1c according to the present embodiment. As shown in FIG. 26, data stored in the combining rule database 45 is represented in a matrix format. The identification result combining unit 70 refers to the combining rule database 45 and identifies the behavior of the whole body of the target using combinations of identification results of the action of the core of the body and identification results of the action of hands.

The behavior identification device 1c according to the present embodiment operates as described above. The behavior identification device 1c according to the present embodiment can identify the behavior of the whole body of a target with higher accuracy by combining an identification result of an action of the core of the target's body with an identification result of an action of the target's hands.

Fourth Embodiment

A fourth embodiment of the present invention relates to an air conditioner that identifies a biological index corresponding to a behavior of a person by using a sensor such as an acceleration sensor, an angular velocity sensor, or a heart rate sensor so as to control an operation of an outdoor unit or an indoor unit, thus achieving more comfortable control. Examples of the biological index include an exercise intensity index and a stress index. FIG. 27 shows an example of a configuration of an air conditioner 200 according to the fourth embodiment of the present invention. As shown in FIG. 27, the air conditioner 200 includes a behavior identification device 1d, an indoor unit 7, an outdoor unit 8, a control rule database 46a, and a control information output unit 80. A sensor 2 and an input unit 4 are connected to the air conditioner 200.

The behavior identification device 1d is substantially the same as the behavior identification device 1 according to the first embodiment shown in FIG. 1 except for the data structure of a component ratio database 43c. In the behavior identification device 1 according to the first embodiment, the component ratio database 43 stores therein a behavior label of a target when each sensor value distribution is measured in association with a component ratio. On the other hand, in the behavior identification device 1d according to the present embodiment, the component ratio database 43c stores therein a biological index of a target when each sensor value distribution is measured in association with a component ratio. Details thereof are described later.

FIG. 28 is a diagram for explaining a usage example of the air conditioner 200 according to the present embodiment. The sensor 2 is attached to a target and wirelessly transmits a measured sensor value to the behavior identification device 1d. The behavior identification device 1d is built or incorporated in the indoor unit 7. While the control rule database 46a and the control information output unit 80 are not shown in FIG. 28, the control rule database 46a and the control information output unit 80 may be incorporated in selected appropriate locations. For example, the control rule database 46a and the control information output unit 80 may be built in the behavior identification device 1d or in the indoor unit 7.

The sensor 2 is a three-axis acceleration sensor. As shown in FIG. 28, the sensor 2 is attached to the waist of a target 400 and measures three-axis acceleration values ax, ay, and az for a behavior of the target 400. In addition, the sensor 2 calculates a norm |a| of the three-axis acceleration values ax, ay, and az by the above formula (1), and outputs the norm every 50 milliseconds. While the present embodiment describes a case where a three-axis acceleration sensor functioning as the sensor 2 is attached to the waist of the target 400, the present invention is not limited thereto. The sensor 2 may be any sensor that can measure a certain change amount relating to a behavior of a target as a sensor value. In addition to the three-axis acceleration sensor, for example, an angular velocity sensor, a position sensor, an air pressure sensor, or a heart rate sensor can be used as the sensor 2.

Next, the behavior identification device 1d according to the present embodiment is described. In particular, differences between the behavior identification device 1d according to the present embodiment and the behavior identification device 1 according to the first embodiment are mainly described. As described above, in the behavior identification device 1d according to the present embodiment, the component ratio database 43c stores therein a biological index corresponding to a behavior of the target 400 when a sensor value distribution is calculated in a generation phase. FIG. 29 is a diagram for explaining a data structure of the component ratio database 43c in the air conditioner 200 according to the present embodiment. The component ratio database 43c stores therein a set $\theta_d$ of component ratios and a biological index in association with a data number d of a sensor value distribution. In the air conditioner 200 according to the present embodiment, the component ratio database 43c uses a biological index as a behavior label.

In the example of FIG. 29, the component ratio database 43c stores therein a METs (Metabolic equivalents) value, which is an exercise intensity index, as a biological index. The METs indicates the exercise intensity as the ratio of metabolic rate (rate of energy consumption) to the reference, which is 1.0 METs (a state where a target is at rest such as lying or sitting). For example, the exercise intensity during walking is approximately 2.5 METs, which is 2.5 times higher rate of metabolism (rate of energy consumption) than that at rest. In addition thereto, METs values for various behaviors are known. For example, the exercise intensity during running at 8.0 km/h is approximately 8.0 METs, and the exercise intensity during doing the first radio exercise is 4.0 METs. An identification unit 22 calculates the similarity between a set of component ratios calculated by a ratio calculating unit 21 and each set of component ratios stored in the component ratio database 43c. In addition, the identification unit 22 outputs, as an identification result, a biological index corresponding to a set of component ratios with the highest similarity among sets of component ratios stored in the component ratio database 43c. The differences between the behavior identification device 1 according to the first embodiment and the behavior identification device 1d according to the present embodiment are as described above.

Next, the control rule database 46a is described. The control rule database 46a stores therein a rule for controlling the indoor unit 7 or the outdoor unit 8 in association with a biological index output from the behavior identification device 1d. FIG. 30 is a diagram for explaining a data structure of the control rule database 46a in the air conditioner 200 according to the present embodiment. For example, the behavior with an exercise intensity of less than 1.0 METs includes lying at rest or sleeping. In this case, it is highly possible that the target 400 is sleeping. The control rule database 46a thus stores therein "not directly blowing on target" as the control rule for an exercise intensity of less than 1.0 METs. For example, the behavior with an exercise intensity of 8.0 METs or more includes a hard exercise such as running at 8.0 km/h. In this case, it is highly possible that the target 400 is doing a hard exercise. The control rule database 46a thus stores therein "directly blowing on target"

as the control rule for an exercise intensity of 8.0 METs or more. In addition, the control rule database 46a stores therein "same as normal state" as the control rule for an exercise intensity of 1.0 METs or more and less than 8.0 METs.

Next, the control information output unit 80 is described. The control information output unit 80 receives a biological index output from the identification unit 22 as an input and refers to the control rule database 46a to determine a control rule, and outputs the control rule to the indoor unit 7 or the outdoor unit 8 as control information. For example, in the example of the control rule shown in FIG. 30, when the identification unit 22 identifies the exercise intensity to be 3.0 METs, the control information output unit 80 refers to the control rule database 46a and outputs the control rule "same as normal state". When the identification unit 22 identifies the exercise intensity to be 9.0 METs, the control information output unit 80 refers to the control rule database 46a and outputs the control rule "directly blowing on target". The indoor unit 7 or the outdoor unit 8 operates according to the control information output from the control information output unit 80. The air conditioner 200 according to the present embodiment operates as described above.

The air conditioner 200 according to the present embodiment identifies a behavior of a person and outputs a biological index corresponding to an identified behavior. It is thus possible to achieve a more comfortable air conditioner control system that directly blows on a person doing a hard exercise or that does not directly blow on a sleeping person.

While the present embodiment describes a case where, for example, a three-axis acceleration sensor is attached to the waist of a target and METs, which is an exercise intensity index, is used as a biological index, the present invention is not limited thereto. For example, a heart rate/pulse sensor may be attached to the chest or wrist of a target and LF/HF, which is a stress index, may be used as a biological index, so that it is possible to achieve a more comfortable air conditioner. LF/HF is a stress index for measuring the balance of an autonomic nervous function, that is, the balance between a Low Frequency (LF) component and a High Frequency (HF) component in heart rate variability. The LF/HF decreases when a person is relaxed and increases when the person gets stressed. Consequently, when the LF/HF is increased, for example, an air conditioner blows air in a fluctuation mode or emits an aromatic fragrance with relaxing effect, so that more comfortable control is achieved.

Fifth Embodiment

A fifth embodiment of the present invention relates to a robot control device that uses a sensor such as an acceleration sensor, an angular velocity sensor, or a heart rate sensor to identify a behavior of an operator around a robot in a factory, and controls an operation of the robot based on an identification result. The robot control device according to the present embodiment identifies a safe behavior that is set in advance as a behavior of a target, a dangerous behavior that is set in advance, and a deviant behavior that is not set in advance to control the operation of the robot. The robot control device according to the present embodiment thus enables a robot system that improves the safety of an operator and prevents a robot from unnecessarily stopping to be established.

Figure 31:
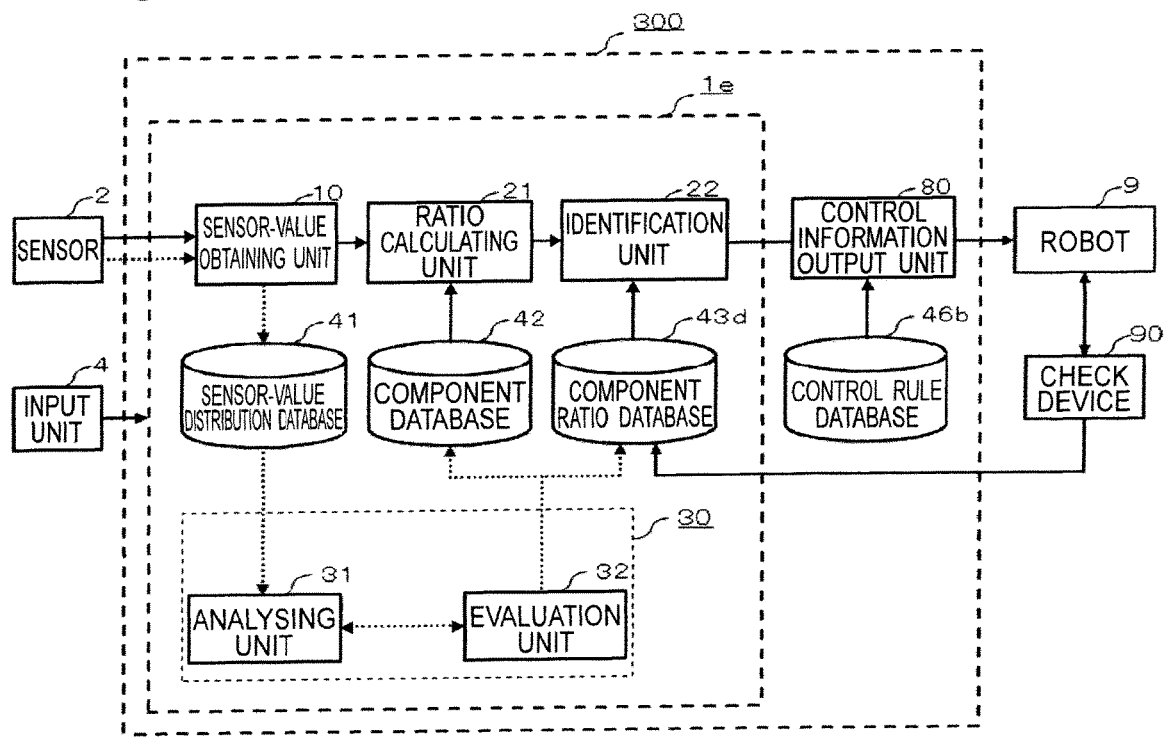
FIG. 31 shows an example of a configuration of a robot control device according to a fifth embodiment of the present invention.

FIG. 31 shows an example of a configuration of a robot control device 300 according to the fifth embodiment of the present invention. As shown in FIG. 31, the robot control device 300 includes a behavior identification device 1e, a control rule database 46b, and control information output unit 80. A sensor 2, an input unit 4, a robot 9, and a check device 90 are connected to the robot control device 300. A robot system is constituted by the robot control device 300, the sensor 2, the input unit 4, the robot 9, and the check device 90. The behavior identification device 1e is substantially the same as the behavior identification device 1 according to the first embodiment shown in FIG. 1 except that the check device 90 can update data in a component ratio database 43d. Details thereof are described later.

Figure 32:
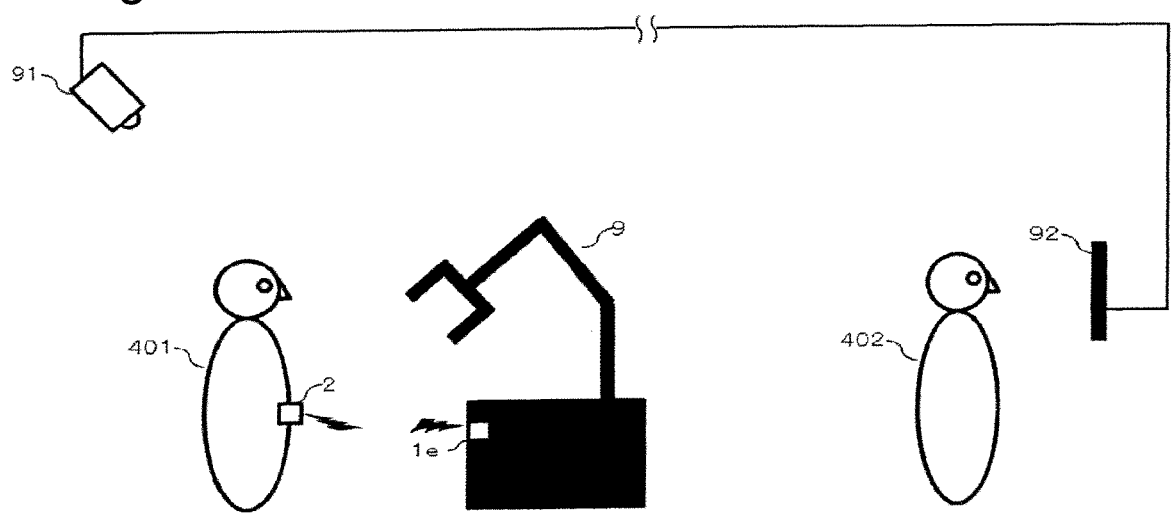
FIG. 32 is a diagram for explaining a usage example of the robot control device according to the fifth embodiment of the present invention.

FIG. 32 is a diagram for explaining a usage example of the robot control device 300 according to the present embodiment. The sensor 2 is attached to an operator 401 and wirelessly transmits a measured sensor value to the behavior identification device 1e. The behavior identification device 1e is built or incorporated in the robot 9. The check device 90 is constituted by a camera 91 and a display device 92. The camera 91 captures images around the robot 9. The display device 92 includes a liquid crystal display device or the like, and displays images captured by the camera 91 in a real-time manner. A third person 402 uses the display device 92 to check the robot 9 and the operator 401. The display device 92 also includes a function of updating data in the component ratio database 43d by an operation of the third person 402. While the control rule database 46b and the control information output unit 80 are not shown in FIG. 32, the control rule database 46b and the control information output unit 80 may be incorporated in selected appropriate locations.

The sensor 2 is a three-axis acceleration sensor in the present embodiment. As shown in FIG. 32, the sensor 2 is attached to the waist of the operator 401 and measures three-axis acceleration values ax, ay, and az for a behavior of the operator 401. In addition, the sensor 2 calculates a norm |a| of the three-axis acceleration values ax, ay, and az by the above formula (1), and outputs the norm every 50 milliseconds. While the present embodiment describes a case where a three-axis acceleration sensor functioning as the sensor 2 is attached to the waist of the operator 401, the present invention is not limited thereto. The sensor 2 may be any sensor that can measure a certain change amount relating to a behavior of a target as a sensor value. In addition to the three-axis acceleration sensor, for example, an angular velocity sensor, a position sensor, an air pressure sensor, or a heart rate sensor can be used as the sensor 2.

Next, the behavior identification device 1e according to the present embodiment is described. In particular, differences between the behavior identification device 1e according to the present embodiment and the behavior identification device 1 according to the first embodiment are mainly described. A sensor-value distribution database 41 stores therein a sensor value distribution measured when the operator 401 takes a safe behavior and a sensor value distribution measured when the operator 401 takes a dangerous behavior. The safe behavior is a behavior that is performed as a normal process operation by the operator 401 around the robot 9. The dangerous behavior is a behavior that is defined in advance to be apparently dangerous to the operator 401 when performed around the robot 9. The component ratio database 43d stores therein "safe behavior" or "dangerous behavior" as a behavior label of the operator 401 when a sensor value distribution is measured. FIG. 33 is a diagram for explaining a data structure of the component ratio database 43d in the robot control device 300 according to the present embodiment.

An identification unit 22 calculates the similarity between a set of component ratios calculated by a ratio calculating unit 21 and each set of component ratios stored in the component ratio database 43d. In addition, the identification unit 22 outputs, as an identification result, a behavior label corresponding to a set of component ratios with the highest similarity among sets of component ratios stored in the component ratio database 43d. However, if the calculated highest similarity is less than a threshold defined in advance, the identification unit 22 outputs "deviant behavior" as an identification result. Therefore, the identification unit 22 outputs any one of "safe behavior", "dangerous behavior", or "deviant behavior" as an identification result. The behavior identification device 1e operates as described above.

Next, the control rule database 46b is described. The control rule database 46b stores therein a rule for controlling the robot 9 in association with an identification result output from the behavior identification device 1e. FIG. 34 is a diagram for explaining a data structure of the control rule database 46b in the robot control device according to the present embodiment. As described above, the safe behavior is a behavior that is performed as a normal process operation by the operator 401 around the robot 9. Consequently, when the identification result is "safe behavior", it is less possible that an operation of the robot 9 endangers the operator 401. The control rule database 46b thus stores therein "normal operation" as the control rule for "safe behavior".

On the other hand, the dangerous behavior is a behavior that is defined in advance to be apparently dangerous to the operator 401 when performed around the robot 9. Consequently, the control rule database 46b stores therein "emergency stop" as the control rule for "dangerous behavior". When the identification result is "deviant behavior", it is highly possible that a behavior that is not classified in advance into a safety behavior or a dangerous behavior is performed. The behavior of the operator 401 in such a case is different from the behavior that is performed as a normal process operation, and is not the behavior that is defined in advance to be apparently dangerous to the operator 401. Consequently, the control rule database 46b stores therein "reduce operating speed" and "ask for check-up" as the control rule for "deviant behavior".

Next, the control information output unit 80 is described. The control information output unit 80 receives a behavior label identified by the identification unit 22 as an input and refers to the control rule database 46a to output a control rule to the robot 9 as control information. For example, when "deviant behavior" is identified by the identification unit 22, the control information output unit 80 outputs the control rule "reduce operating speed" and "ask for check-up". The robot 9 operates according to input control information. When "ask for check-up" is input as the control information, the robot 9 outputs a signal asking for checking the state of the operator 401 and the robot 9 through a wireless or wired communication unit to the check device 90.

Next, the check device 90 is described. The check device 90 includes the camera 91 and the display device 92. When a signal asking for checking the state is input from the robot 9 to the check device 90, the check device 90 captures images around the robot 9 using the camera 91 and displays the images on the display device 92 in a real-time manner. The third person 402 can thus check a deviant behavior of the operator 401 around the robot 9 and handle the deviant behavior as needed. When the third person 402 checks that the deviant behavior of the operator 401 is apparently dangerous to the operator 401, the third person 402 can emergently stop the robot 9. Alternatively, when the third person 402 checks that the deviant behavior of the operator 401 is not dangerous to the operator 401, the third person 402 can reduce an operating speed and cause the operating robot 9 to return to its normal operation.

Additionally, when the third person 402 checks that the deviant behavior of the operator 401 is apparently dangerous to the operator 401, the check device 90 associates a set of component ratios calculated by the ratio calculating unit 21 with the label "dangerous behavior" and adds the set of component ratios to the component ratio database 43d. Moreover, when the third person 402 checks that the behavior that is identified to be the deviant behavior of the operator 401 is misdetected as the behavior performed as a normal process operation by the operator 401, the check device 90 associates a set of component ratios calculated by the ratio calculating unit 21 with the "safe behavior" label and adds the set of component ratios to the component ratio database 43d.

While the present embodiment describes a case where for example, a three-axis acceleration sensor is attached to the waist of the operator 401, the present invention is not limited thereto. A heart rate/pulse sensor may be attached to the chest or wrist of the operator 401 to directly identify physiological abnormality of the operator 401, so that it is possible to achieve a safer robot system. The robot control device 300 according to the present embodiment identifies a behavior of the operator 401 operating around the robot 9 in a factory and controls an operation of the robot based on an identification result, and thus it is possible to improve the safety of an operator. For example, when a dangerous behavior of the operator 401 is identified, the robot 9 emergently stops. Consequently, it is possible to reduce the probability that the operator 401 is endangered. In addition, when a deviant behavior of the operator 401 is identified, the third person 402 checks the danger to the operator 401 and handles the danger. Consequently, it is possible to prevent the robot from unnecessarily stopping and improve the safety of the operator 401. Moreover, when the deviant behavior of the operator 401 is identified, an identification result and an actual behavior of the operator 401 are checked and additionally stored in a database. Consequently, it is possible to improve the identification performance.

DESCRIPTION OF REFERENCE SYMBOLS 1, 1b, 1c, 1d, 1e behavior identification device
2, 2a, 2b sensor
3 display unit
4 input unit
5 mode detecting unit
7 indoor unit
8 outdoor unit
9 robot
10 sensor-value obtaining unit
21 ratio calculating unit
22 identification unit
30, 30b basic distribution generating unit
31 analysing unit
32 evaluating unit
41, 41b sensor-value distribution database
42 component database
43, 43b, 43c, 43d component ratio database
44 mode corresponding database
45 combining rule database
46a, 46b control rule database
61 component integrating unit
62 component select unit
63 ratio select unit
70 identification result combining unit 80 control information output unit
90 check device
91 camera
92 display device
100a, 100b operation identifying unit
200 air conditioner
300 robot control device
400 target
401 operator
402 third person
1001 processing circuit
1002, 1005 memory
1003 data bus
1004 processor

The invention claimed is:

1. An air conditioner comprising:
a behavior identification device that identifies a behavior of a target using a sensor value measured by a sensor for the behavior of the target, the behavior identification device including:
  processing circuitry configured to obtain the sensor value and calculate a sensor value distribution that is a distribution of the sensor value measured within a predetermined time,
  a component memory that stores therein a set of basic distributions that are basic components constituting the sensor value distribution, and
  a component ratio memory, wherein
the processing circuitry is configured to calculate a first component ratio that is a ratio of each of the basic distributions included in the sensor value distribution,
the component ratio memory stores therein a second component ratio that is the ratio determined in association with a behavior to be identified,
the processing circuitry is configured to compare the first component ratio to the second component ratio to identify the behavior,
the basic distribution is calculated as a sensor value distribution that is a base when each sensor value distribution is assumed to be a vector based on a set of the sensor value distributions obtained in advance for each of a plurality of types of the behavior, and
the air conditioner identifies a biological index corresponding to the behavior of the target to control an operation of an outdoor unit or an indoor unit.

2. The air conditioner according to claim 1, wherein the processing circuitry is configured to calculate the basic distribution and control storing of the basic distribution in the component memory.

3. The air conditioner according to claim 2, wherein the processing circuitry is configured to store a ratio of each of the basic distributions included in the sensor value distribution obtained in advance and control storing of the ratio in the component ratio memory in association with the behavior when the sensor value is obtained.

4. The air conditioner according to claim 3, wherein the processing circuitry is configured to
  estimate the basic distribution and a ratio of each of the basic distributions included in the sensor value distribution obtained in advance, and
  evaluate the basic distribution and the ratio that are estimated and control storing of the basic distribution in the component database only when an evaluation result satisfies a predetermined evaluation criteria.

5. The air conditioner according to claim 4, wherein the processing circuitry is configured to calculate an average value of a ratio of the basic distribution included in the sensor value distribution obtained in advance for each of the basic distributions, and determine that an evaluation result satisfies the evaluation criteria when all of the average values calculated exceed a predetermined ratio.

6. The air conditioner according to claim 5 wherein the processing circuitry is configured to detect a behavior mode of a target, and calculate the basic distribution for each behavior mode based on the sensor value distribution obtained for each behavior mode of the target.

7. The air conditioner according to claim 4, wherein the processing circuitry is configured to detect a behavior mode of a target, and calculate the basic distribution for each behavior mode based on the sensor value distribution obtained for each behavior mode of the target.

8. The air conditioner according to claim 3, wherein the processing circuitry is configured to detect a behavior mode of a target, and calculate the basic distribution for each behavior mode based on the sensor value distribution obtained for each behavior mode of the target.

9. The air conditioner according to claim 8, wherein the processing circuitry is configured to compare the basic distributions calculated in different behavior modes and integrate a plurality of the basic distributions that are similar to each other.

10. The air conditioner according to claim 2, wherein the processing circuitry is configured to
  estimate the basic distribution and a ratio of each of the basic distributions included in the sensor value distribution obtained in advance, and
  evaluate the basic distribution and the ratio that are estimated and control storing of the basic distribution in the component memory only when an evaluation result satisfies a predetermined evaluation criteria.

11. The air conditioner according to claim 10, wherein the processing circuitry is configured to calculate an average value of a ratio of the basic distribution included in the sensor value distribution obtained in advance for each of the basic distributions, and determine that an evaluation result satisfies the evaluation criteria when all of the average values calculated exceed a predetermined ratio.

12. The air conditioner according to claim 11, wherein the processing circuitry is configured to detect a behavior mode of a target, and calculate the basic distribution for each behavior mode based on the sensor value distribution obtained for each behavior mode of the target.

13. The air conditioner according to claim 10, wherein the processing circuitry is configured to detect a behavior mode of a target, and calculate the basic distribution for each behavior mode based on the sensor value distribution obtained for each behavior mode of the target.

14. The air conditioner according to claim 2, wherein the processing circuitry is configured to detect a behavior mode of a target, and calculate the basic distribution for each behavior mode based on the sensor value distribution obtained for each behavior mode of the target.

15. The air conditioner according to claim 14, wherein the processing circuitry is configured to compare the basic distributions calculated in different behavior modes and integrate a plurality of the basic distributions that are similar to each other.

16. The air conditioner according to claim 1, wherein the processing circuitry is configured to detect a behavior mode of a target, and calculate the basic distribution for each behavior mode based on the sensor value distribution obtained for each behavior mode of the target.

17. The air conditioner according to claim 16, wherein the processing circuitry is configured to compare the basic distributions calculated in different behavior modes and integrate a plurality of the basic distributions that are similar to each other.

18. The air conditioner according to claim 1 wherein the processing circuitry is configured to
obtain the sensor value from each of different sensors, and
identify a behavior based on a plurality of identification results.

19. A robot control device comprising:
a behavior identification device that identifies a behavior of a target using a sensor value measured by a sensor for the behavior of the target, the behavior identification device including:
processing circuitry configured to obtain the sensor value and calculate a sensor value distribution that is a distribution of the sensor value measured within a predetermined time,
a component memory that stores therein a set of basic distributions that are basic components constituting the sensor value distribution, and
a component ratio memory, wherein
the processing circuitry is configured to calculate a first component ratio that is a ratio of each of the basic distributions included in the sensor value distribution,
the component ratio memory stores therein a second component ratio that is the ratio determined in association with a behavior to be identified,
the processing circuitry is configured to compare the first component ratio to the second component ratio to identify the behavior,
the basic distribution is calculated as a sensor value distribution that is a base when each sensor value distribution is assumed to be a vector based on a set of the sensor value distributions obtained in advance for each of a plurality of types of the behavior, and
the robot control device identifies a safe behavior that is set in advance as the behavior of the target, a dangerous behavior that is set in advance, and a deviant behavior that is not set in advance to control an operation of a robot based on an identification result.

* * * * *